United States Patent [19]

Mathur et al.

[11] Patent Number: 4,547,514
[45] Date of Patent: Oct. 15, 1985

[54] ARYLOXY-N-(AMINOALKYL)-1-PYRROLIDINE AND PIPERIDINE CARBOXAMIDES AND CARBOTHIOAMIDES HAVING ANTIARRHYTHMIC ACTIVITY

[75] Inventors: Pershottam P. Mathur, Midlothian; William L. Smith, Richmond, both of Va.

[73] Assignee: A. H. Robins Company, Incorporated, Richmond, Va.

[21] Appl. No.: 557,885

[22] Filed: Dec. 5, 1983

[51] Int. Cl.[4] ............... A61K 31/445; A61K 31/535; A61K 31/495; A61K 31/385
[52] U.S. Cl. .................... 514/327; 514/228; 514/235; 514/252; 514/316; 514/319; 514/326; 514/422; 514/423; 514/821
[58] Field of Search ............ 424/274, 267, 250, 248.5, 424/248.54

[56] References Cited
U.S. PATENT DOCUMENTS 3,577,415 5/1971 Cale .................................. 260/247.2
4,036,957 7/1977 Alphin et al. ....................... 424/232
4,075,340 2/1978 Maffrand ............................. 424/256

OTHER PUBLICATIONS

*Journal of Medicinal Chemistry*, 1974, vol. 17, No. 9, 1000–1008.
*Metabolism and Disposition*, vol. 4, No. 4, 1976, 379–386.

Primary Examiner—Frederick E. Waddell

[57] ABSTRACT

Pharmaceutical compositions comprised of aryloxy-N-(aminoalkyl)-1-pyrrolidine and piperidine carboxamides and carbothioamides are provided of the formula:

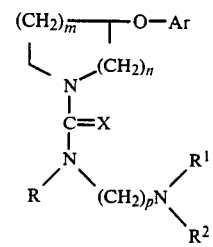

wherein Ar is selected from the group consisting of 1-naphthyl, 2-naphthyl, 2,3-dihydro-1H-inden-4-yl, 2,3-dihydro-1H-inden-5-yl, phenyl, substituted phenyl wherein the substituents are selected from lower alkyl of from 1 to 8 carbon atoms, lower alkyloxy of from 1 to 8 carbon atoms, halogen and trifluoromethyl; m and n are 1 or 2 but are never 2 at the same time; p is 1, 2, 3 or 4; R is selected from hydrogen or lower alkyl of from 1 to 3 carbon atoms; $R^1$ and $R^2$ are selected from hydrogen, lower alkyl of from 1 to 8 carbon atoms, phenyl, phenyl lower alkyl of from 7 to 9 carbon atoms, and cycloalkyl of from 3 to 8 carbon atoms, and $R^1$ and $R^2$ taken together with the adjacent atom may form a heterocyclic residue selected from 4-morpholino, 1-pyrrolidino, 1-piperidino, 1-piperazino and 4-lower alkyl piperazin-1-yl; X is oxygen or sulfur; and the pharmaceutically acceptable acid addition salts thereof having antiarrhythmic activity.

21 Claims, No Drawings

ARYLOXY-N-(AMINOALKYL)-1-PYRROLIDINE AND PIPERIDINE CARBOXAMIDES AND CARBOTHIOAMIDES HAVING ANTIARRHYTHMIC ACTIVITY

BACKGROUND OF THE INVENTION

The present invention relates to pharmaceutical compositions comprised of certain 3-aryloxy-N-(aminoalkyl-1-pyrrolidine and piperidine carboxamides and carbothioamides and pharmaceutically acceptable acid addition salts thereof and methods of use thereof in the treatment of antiarrhythmic activity.

Compounds of the formula:

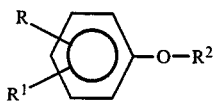

are disclosed in commonly-assigned U.S. Pat. No. 4,036,957 wherein R is selected from hydrogen, halogen, lower alkyl, lower alkoxy or trifluoromethyl; $R^1$ is selected from hydrogen, halogen, lower alkyl or lower alkoxy; and $R^2$ may be, for example,

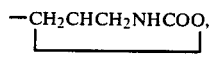

More specifically, the patent discloses the compound:

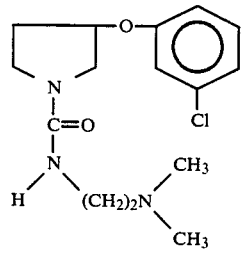

for use in compositions for the reduction of gastric bleeding during aspirin therapy for inflammation.

Compounds of the formula:

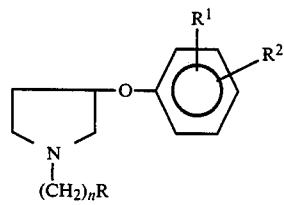

are also disclosed in commonly-assigned U.S. Pat. No. 3,577,432 wherein R represents lower alkyl, lower alkoxy, lower alkenyl, lower alkynyl, carbonyl, carbonoyloxy, phenoxy, benzyloxy, alpha-hydroxybenzyl, styryl, hydroxy, 1,2-dihydroxyethyl, amidino, carbalkoxy, and phenyl when n is zero; $R^1$ and $R^2$ represent hydrogen, lower alkyl, lower alkoxy, trifluoromethyl, acetyl, and halogen having an atomic weight less than 80; and n is zero to four and acid addition salts thereof.

Compounds of the formula:

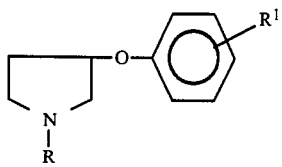

are also known as described in German Pat. No. 1,964,510 in which R is benzyl, methyl or carbamoyl; and $R^1$ is carbamoyl, carboxyl, aminocarbonyl, amino, subst. benzamidoethyl, aminomethyl, hydroxymethyl, lower alkoxycarbonyl, cyano, lower alkylcarbonyl, acetamido, benzamido, or carbamoylamino.

Compounds of the formula

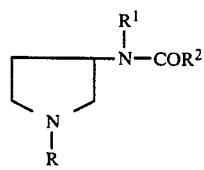

are known as described in German Pat. No. 1,964,516 wherein R is hydrogen, lower alkyl, allyl, phenyl, phenoxy-lower alkyl, cyclohexyl, or phenyl-lower alkyl; $R^1$ is hydrogen, lower alkyl, phenyl, cyclohexyl, lower alkoxyphenyl, hydroxyphenyl, halophenyl, or trifluoromethylphenyl; and $R^2$ is lower alkyl, phenyl, nitrophenyl, aminophenyl, halophenyl, lower alkoxyphenyl, phenoxy-lower alkyl, halophenoxy-lower alkyl, lower alkylphenyl, or trifluoromethylphenyl.

Compounds of the formula:

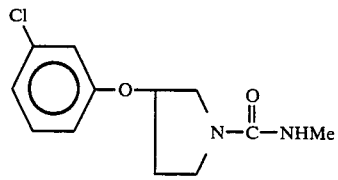

are known as disclosed in Drug Metab. Disp., 1976, 4(4), pp. 379–386.

Compounds of the formula:

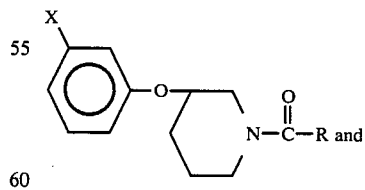

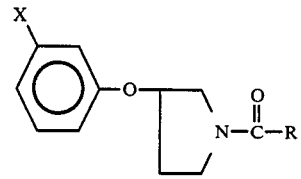

are disclosed in *Journal of Medicinal Chemistry*, 1974 Vol. 17, No. 9, pp. 1000–1008, wherein R may be NHCH$_3$, N(CH$_3$)$_2$, NHC$_2$H$_5$, NHC$_6$H$_5$, NHC$_6$H$_4$-4-OCH$_3$, N(C$_6$H$_5$)$_2$, NH$_2$, NHC$_6$H$_4$-3-Cl, among others.

SUMMARY OF THE INVENTION

The present invention is directed to aryloxy-N-(aminoalkyl)-1-pyrrolidine and piperidine carboxamides and carbothioamides, compositions containing the same as active ingredients and methods of use thereof in controlling cardiac arrhythmia, said compounds having the formula:

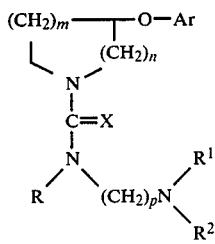

(I)

wherein
Ar is selected from the group consisting of 1-naphthyl, 2-naphthyl, 2,3-dihydro-1H-inden-4-yl, 2,3-dihydro-1H-inden-5-yl, phenyl, substituted phenyl wherein the substituents are selected from lower alkyl of from 1 to 8 carbon atoms, lower alkyloxy of from 1 to 8 carbon atoms, halogen and trifluoromethyl;
m and n are 1 or 2 but are never 2 at the same time;
p is 1, 2, 3 or 4;
R is selected from hydrogen or lower alkyl of from 1 to 3 carbon atoms;
R$^1$ and R$^2$ are selected from hydrogen, lower alkyl of from 1 to 8 carbon atoms, phenyl, phenyl lower alkyl of from 7 to 9 carbon atoms, and cycloalkyl of from 3 to 8 carbon atoms, and R$^1$ and R$^2$ taken together with the adjacent atom may form a heterocyclic residue selected from 4-morpholino, 1-pyrrolidino, 1-piperidino, 1-piperazino and 4-lower alkyl piperazin-1-yl;
and the pharmaceutically acceptable acid addition salts thereof.

DETAILED DESCRIPTION OF THE INVENTION

The compounds described hereinafter and represented by Formula I have been shown by acceptable pharmacological procedures to have utility as physiologically active agents. Such compounds are therapeutically applicable in the treatment of cardiac arrhythmias.

In the definitions of the symbols as they appear in Formula I and elsewhere in this specification, the terms below shall have the noted significance.

The term "lower alkyl" as used herein includes straight and branched chain radicals. Examples of lower alkyl radicals suitable for use in the present invention include methyl, ethyl, propyl, n-butyl, isopropyl, isobutyl, amyl, isoamyl, hexyl, heptyl, octyl, isooctyl (insofar as it conforms to the scope of lower alkyl employed in Formula I).

The term "phenyl lower alkyl" as used herein includes groups such as benzyl, phenethyl, 1-phenylethyl, phenpropyl, etc. wherein "lower alkyl" is as defined above.

The term "substituted phenyl" comprises both the substituted phenyl radical and the disubstituted phenyl radical. The substituted phenyl radicals have preferably one or two substituents (as defined) and furthermore, the substituents can be in various available positions of the phenyl nucleus and, when more than one substituent is present, can be the same or different and can be in various combinations relative to each other. The lower alkyl and alkyloxy substituents each have preferably 1 to 4 carbon atoms which can be arranged either as straight or branched chains. A total of 9 carbon atoms in all ring substituents, making a total of 15 carbon atoms in the radical, is the preferred maximum.

The compounds of the present invention may be conveniently employed in the form of pharmaceutically acceptable acid addition salts. Appropriate acid addition salts are those derived from mineral acids such as hydrochloric, hydrobromic, sulfuric, and phosphoric; and organic acids such as acetic, citric, lactic, maleic, oxalic, fumaric, and tartaric. The preferred acid addition salt is the hydrochloride. The salts are conveniently prepared by reaction of the basic compounds with the selected acid, either or both of which may be in the form of ether, alcohol, or acetone solutions.

Pharmacology

The compounds of the present invention are demonstrated to exhibit antiarrhythmic activity wherein the arrhythmia is induced by (1) ouabain, (2) coronary artery ligation, or (3) injury as discussed in greater detail below, with the results of the tests set forth in Table 1.

1. Quabain-Induced Arrhythmias

The antiarrhythmic activity of certain of the novel compounds of the present invention was demonstrated using the following procedure. Adult mongrel dogs of either sex weighing from 8 to 14 kg were used under barbituate anesthetic. A Grass Model 7 polygraph was used for recording femoral arterial blood pressure (Statham P23AC Transducer) and the electrocardiagram (Grass 7P4 Preamplifier). Quabain was given intravenously in an initial dose of 40 µg/kg, in a second dose of 20 µg/kg given 30 minutes later and in subsequent doses of 10 µg/kg which were repeated at 15 minute intervals for producing cardiac arrhythmias that persisted for at least 15 minutes. When the arrhythmias were established, the test compounds were administered by infusion (Harvard Model 942 Infusion Pump) into a femoral vein at a rate of 1 mg/kg/min. Concentrations of compounds were adjusted according to the weight of the dog to allow a volume infusion of 1 ml/min. Compounds that are considered to be active as antiarrhythmic agents elicit reversion of the arrhythmia to sinus rhythm for at least 30 minutes.

2. Coronary Artery Ligation-Induced Arrhythmias

Adult mongrel dogs which are in the conscious state were used for the test and cardiac arrhythmias were induced by prior (22–24 hr) surgical preparation in which blood flow through a coronary artery was occluded by use of a constrictor device. A Grass Model 79 polygraph was used for recording the electrocardiogram (Grass 7P4 Preamplifier).

The test compound was administered by infusion (Harvard Model 942 Infusion Pump) into a saphenous vein to one group of dogs at a rate of 0.5 mg/kg/min. Concentration of the compounds was adjusted according to the weight of the dog to allow a volume of infusion of 0.5 ml/min. Heart rate, number of ectopic cardiac beats per minute, and the percent ectopic beats (Ectopic beats/hr.×100) were recorded for the pretreatment period and after every 2-min interval of test compound infusion. Test compound was administered until a total of 20 mg/kg was infused. The test compound was administered orally by gavage to another group of dogs at dose levels of 10 through 40 mg/kg. The test compound was prepared in distilled water to give a total volume of 20 ml. Following the administration of the test compound, the heart rate, number of ectopic cardiac beats per minute, and the percent ectopic beats (Ectopic beats/hr.×100) were recorded at 15 minute intervals. The compound was considered active if it abolished the ectopic ventricular frequency and caused a return to normal sinus rhythm within 2 hours of administration.

3. Injury Stimulus-Induced Arrhythmias

Correction of existing arrhythmias of atrial origin is carried out on adult mongrel dogs which are under barbiturate anesthesia and mechanical respiration (Harvard Respiration Pump Model 6B). During the test a Grass Model 7 polygraph was used for recording femoral arterial blood pressure (Statham P23AC Transducer) and the electrocardiogram (Grass 7P4 Preamplifier). The heart was exposed by an incision at the fourth intercostal space of the right thorax and the right atrium was exposed. A band of right atrial tissue lying between the superior and inferior vena cava was crushed using hemostatic forceps. Atrial arrhythmias were initiated by applying an electrical stimulus of 1 m sec, 20-100 Hz and 3-5 V to the crushed area (Method of Rosenblueth & Garcia-Ramos). When the arrhythmias were established and persisted for at least 15 minutes, the test compound was administered by infusion (Harvard Model 940 Infusion Pump) into a femoral vein at a rate of 1 mg/kg/min. Concentration of the test compound was adjusted according to the weight of the dog to allow a volume infusion of 1 ml/min. The compound was considered active an an antiarrhythmic agent if the induced arrhythmia (atrial flutter or atrial fibrillation) was reverted to a normal sinus rhythm and the atrial frequency is diminished in order that a 1:1 relationship of atrial and of ventricular rate was established.

TABLE 1

Effect of Compounds on Cardiac Arrhythmias in Dogs

| Example No. | Ouabain[1,4] Induced Correcting Dose Range mg/kg, I.V. | Coronary Artery Ligation-Induced[2,4] Correcting Dose Range mg/kg, I.V. | Injury Stimulus-Induced[3,5] Correcting Dose Range mg/kg, I.V. |
|---|---|---|---|
| 1 | 11 | 7-20 | No data |
| 2 | 20 | 6-7 | No data |
| 3 | 9-20 | 9 | No data |
| 4 | 6-20 | No data | No data |
| 5 | 3-11 | No data | No data |
| 6 | 3-17 | 2-10 | No data |
| 7 | 10-12 | No data | 8-9 |
| 8 | 7 | No data | 7 |
| 9 | 15 | No data | 5-17 |
| 10 | No data | No data | 17 |
| 11 | No data | No data | 9-10 |
| 12 | 15 | No data | 13-20 |

TABLE 1-continued

Effect of Compounds on Cardiac Arrhythmias in Dogs

| Example No. | Ouabain[1,4] Induced Correcting Dose Range mg/kg, I.V. | Coronary Artery Ligation-Induced[2,4] Correcting Dose Range mg/kg, I.V. | Injury Stimulus-Induced[3,5] Correcting Dose Range mg/kg, I.V. |
|---|---|---|---|
| 13 | 19 | No data | 19-20 |

[1]Cardiac arrhythmias produced by Method of Lucchessi and Hardman, 1961, J. Pharmacol. Exp. Therap. 132, 373-381.
[2]Cardiac arrhythmias produced by modification of Method of Harris, 1950, Circulation 1, 1318, as reported by Smith et al, 1973, Pharmacologist 15, 192.
[3]Cardiac arrhythmias produced by Method of Rosenblueth and Garcia-Ramos, 1947, Am. Heart. J. 33, 677.
[4]Cardiac arrhythmia of ventricular origin.
[5]Cardiac arrhythmia of arterial origin.

General Preparation

The compounds of the present invention may be prepared by the exemplary methods A and B diagrammed and described below.

Method A: (See U.S. Pat. No. 3,577,432 for preparation of benzyl intermediate and compare Journal of Medicinal Chemistry 1974, Vol. 17, No. 9, pp 1000-1008 for concept of reacting a 1-benzyl-3-phenoxypyrrolidine with phosgene followed by an amine).

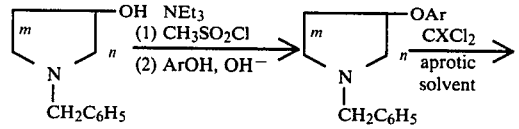

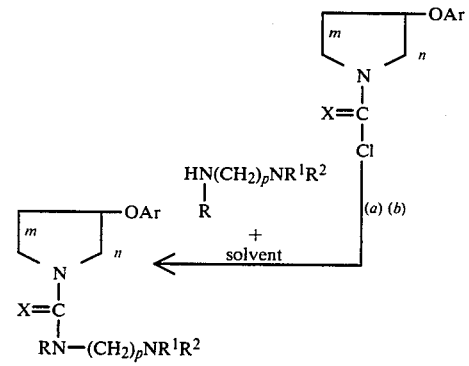

(a)Excess amine or equimolar amount of amine + base and ice water.
(b)With the proviso that when R is not hydrogen, $R^1$ and $R^2$ must be other than hydrogen or R is the same as $R^1$ and $R^2$ is hydrogen.

Method B: (See U.S. Pat. No. 3,577,432, Journal of Medicinal Chemistry, ibid, for preparation of starting materials).

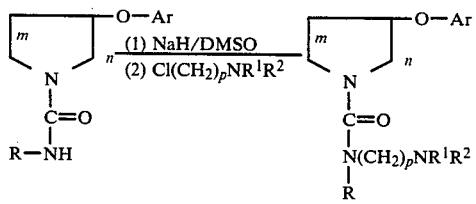

Alternately, compounds of Formula I wherein X=S may be prepared by the exemplary Methods C and D diagrammed and described below.

Method C: (X is S; R is always H).

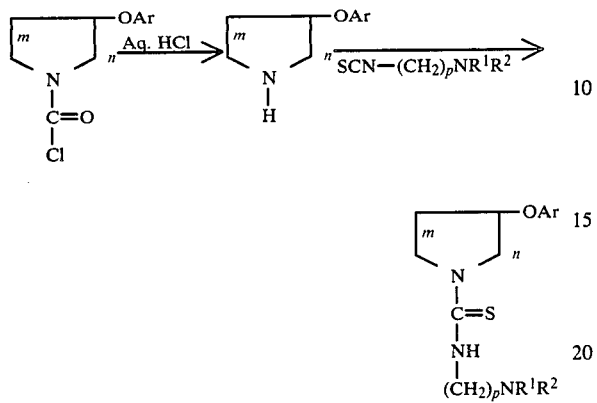

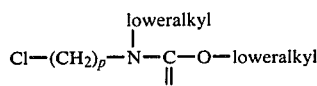

Method D: (X is S; R is other than H).

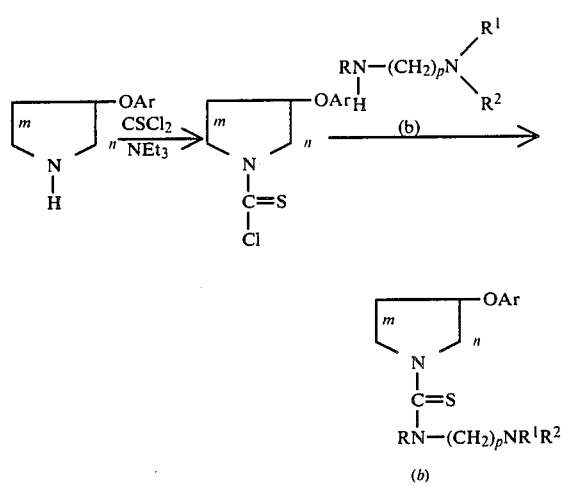

(b)Same proviso as (b) above in Method A.

The amino isothiocyanates used in Method C are either available commercially or may be prepared as represented by the following reaction:

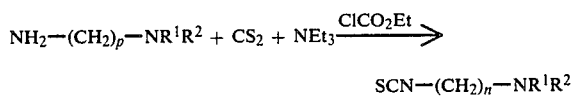

Compounds wherein $R^1$ and $R^2$ are both hydrogen may be prepared via either Methods A or B by substituting the reagent

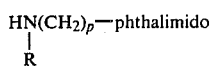

in the last step in Method A or the reagent Cl—(CH$_2$)$_p$-phthalimido in Method B and thereafter reacting the products with hydrazine hydrate.

Compounds wherein $R^1$ and $R^2$ are piperazine unsubstituted in the four position may be prepared using a piperazinyl amine wherein the piperazine radical is blocked in the four position and thereafter hydrolyzing off the protecting group.

Compounds wherein $R^1$ is H and $R^2$ is a methyl radical may be prepared by reacting a compound wherein $R^1$ and $R^2$ are both hydrogen with triethylorthoformate followed by reaction with sodium borohydride, or more generally, a compound wherein $R^1$ is hydrogen and $R^2$ is lower alkyl may be prepared from a compound prepared in Method B wherein $R^1$ is lower alkyl and $R^2$ is —C(O)—O-loweralkyl (by using $$Cl-(CH_2)_p-N-\underset{\underset{O}{\|}}{\overset{loweralkyl}{\overset{|}{C}}}-O-loweralkyl$$

reagent) followed by hydrolysis.

Sources and Preparations of Pyrrolidine and Piperidine Carbonyl Chlorides

Descriptions of the preparation and physical constants of starting compounds used in preparation of precursors were available in U.S. Pat. No. 3,577,432 as follows:

1-benzyl-3-phenoxypyrrolidine fumarate,
1-benzyl-3-(3-trifluoromethylphenoxy)pyrrolidine hydrochloride,
1-benzyl-3-(2-methoxyphenoxy)pyrrolidine (free base),
1-benzyl-3-(3-chlorophenoxy)pyrrolidine hydrochloride,
1-benzyl-3-(2-methylphenoxy)pyrrolidine maleate,
1-benzyl-3-(2-ethoxyphenoxy)pyrrolidine maleate,
1-benzyl-3-(4-methoxyphenoxy)pyrrolidine maleate,
1-benzyl-3-(4-fluorophenoxy)pyrrolidine hydrochloride,
1-benzyl-3-(3,5-dimethylphenoxy)pyrrolidine hydrochloride,
1-benzyl-3-(3-methoxyphenoxy)pyrrolidine maleate,
1-benzyl-3-(4-chlorophenoxy)pyrrolidine hydrochloride,
1-benzyl-3-(4-bromophenoxy)pyrrolidine hydrochloride, and in J. Med. Chem. (1974) 17, No. 9, p. 1000–1008 as follows:
1-benzyl-3-(3,5-dimethylphenoxy)pyrrolidine hydrochloride,
1-benzyl-4-phenoxypyrrolidine (free base),
1-benzyl-4-(4-bromophenoxy)piperidine hydrochloride,
1-benzyl-4-(3-trifluoromethylphenoxy)piperidine hydrochloride,
1-benzyl-4-(4-trifluoromethylphenoxy)piperidine hydrochloride, Additionally, the following starting compounds were prepared and isolated using the techniques of the foregoing references and confirming chemical analysis obtained and melting points obtained as indicated:

1-benzyl-3-(3-methylphenoxy)pyrrolidine fumarate (crude oil),
1-benzyl-3-(3-chloro-4-fluorophenoxy)pyrrolidine monohydrochloride, m.p. 160.5°–161° C.,
1-benzyl-3-(3-trifluoromethylphenoxy)pyrrolidine monohydrochloride, m.p. 165°–166° C.,
1-benzyl-3-(3,4-dichlorophenoxy)pyrrolidine monohydrochloride, m.p. 168.5°–169° C.,
1-benzyl-3-[(2,3-dihydro-1H-inden-4-yl)oxy]pyrrolidine monooxalate, m.p. 170°–171° C.,
1-benzyl-3-(1-naphthalenyloxy)-1-pyrrolidine (free base in crude oil form), 1-benzyl-3-(3-bromophenoxy)pyrrolidine hydrochloride, m.p. 123°–124° C., 1-benzyl-3-(3,5-dichlorophenoxy)pyrrolidine hydrochloride, m.p. softens 175°–177° C. clear amber melt 179° C., 1-benzyl-3-(3,4-dichlorophenoxy)piperidine hydrochloride, m.p. 199°–200° C., 1-benzyl-4-(3,4-dichlorophenoxy)piperidine hydrochloride, m.p. 233–237 (sublimes), 1-benzyl-3-(1-naphthalenyloxy)pyrrolidine, 1-benzyl-3-(2,6-dichlorophenoxy)pyrrolidine hydrochloride, m.p. 171°–172° C.

1-benzyl-3-(2,3-dichlorophenoxy)pyrrolidine hydrochloride, m.p. 154°–155° C.

The foregoing salts were converted to the free bases by proportioning between a suitable solvent such as methylene chloride or benzene and aqueous base and evaporating the solvent layer if necessary to reduce the volume. Complete evaporation gives the pure free base.

Preparations 1–21 & 23 illustrate preparation of aryloxy-1-pyrrolidinecarbonyl (and carbothioyl) chlorides and aryloxy-1-piperidinecarbonyl (and carbothioyl) chlorides and, in addition, Preparation 22 illustrates preparation of aryloxy pyrrolidines also useful in Method D above.

Preparation 1

3-(3-Methylphenoxy)-1-pyrrolidinecarbonyl Chloride

To a stirred solution of 9.5 g (0.097 mole) of phosgene in 100 ml of methylene chloride under nitrogen gas was added dropwise 23.84 g (0.088 mole) of 1-benzyl-3-(3-methylphenoxy)pyrrolidine in 50 ml of methylene chloride. When the addition was complete, thin-layer chromatography showed no starting pyrrolidine remained. The reaction mixture was stirred overnight and concentrated in vacuo to give an oil. The oil was triturated with 30/60 petroleum ether to remove benzyl chloride. A white solid, 14.4 g of crude product was obtained. A portion was recrystallized from hexane.

Analysis: Calculated for $C_{12}H_{14}NO_2Cl$: C,60.13; H,5.89; N,5.84. Found: C,60.10; H,5.90; N,5.79.

Preparation 2

3-(2-Methoxyphenoxy)-1-pyrrolidinecarbonyl Chloride

To a stirred solution of 60 ml of 2 molar phosgene (0.11 mole) in benzene under nitrogen gas was added dropwise a solution of 29.3 g (0.1 mole) of 1-benzyl-3-(2-methoxyphenoxy)pyrrolidine in 100 ml of benzene. The reaction mixture was stirred at ambient temperature for 2 hours and then concentrated in vacuo to give an oil. The oil was triturated with warm 30/60 petroleum ether and the petroleum ether was decanted to remove benzyl chloride. On the third trituration the oil solidified to give 19.65 g of crude product. The combined petroleum ether decantate, on cooling, yielded an additional 4.8 g, m.p. 80°–81° C. The combined yield was 23.45 g (91.7%). Recrystallization of a 1.25 g sample from 25 ml of 30/60 petroleum ether gave fine white crystals, m.p. 80.5°–82° C. The yield of purified product based on this aliquot was 22.6 g (88%).

Analysis: Calculated for $C_{12}H_{14}NO_3Cl$: C,56.37; H,5.52; N,5.48. Found: C,56.39; H,5.52; N,5.44.

Preparation 3

3-(3-Chloro-4-fluorophenoxy)-1-pyrrolidinecarbonyl Chloride

To a stirred solution of 19.6 g (0.2 mole) of phosgene in benzene (100 ml of 2 molar solution) under nitrogen gas was added dropwise 61.1 g (0.2 mole) of 1-benzyl-3-(3-chloro-4-fluorophenoxy)pyrrolidine in 100 ml of dry benzene. The mixture was stirred for about 2½ days. The mixture was filtered to remove 8 g of starting compound as the hydrochloride salt and the filtrate was concentrated under reduced pressure. The resulting oil was triturated in succession with three 100 ml portions of 30/60 petroleum ether. The oil residue was again subjected to reduced pressure to remove petroleum ether. The oil residue, 46 g contained 5–10% benzyl chloride. The combined ether washes yielded 4 g of crystalline product on standing. Yield of product was 50 g (93%)., m.p. 63°–65° C.

Analysis: Calculated for $C_{11}H_{10}Cl_2FNO_2$: C,47.51; H,3.62; N,5.04. Found: C,47.57; H,3.66; N,5.02.

Preparation 4

3-(3,4-Dichlorophenoxy)-1-pyrrolidinecarbonyl Chloride

To a stirred solution of 275 ml of 2 molar phosgene (0.55 mole) in benzene under nitrogen gas was added dropwise a solution of 0.5 mole of 1-benzyl-3-(3,4-dichlorophenoxy)pyrrolidine in 200 ml of dry benzene. The reaction mixture was stirred an additional 0.5 hr, then was filtered to remove 10 g of the starting pyrrolidine compound as the hydrochloric acid salt. The filtrate was concentrated under reduced pressure to give an oil. The oil was triturated four times in succession with 200 ml each of 30/60 petroleum ether which removed most of the benzyl chloride by-product. The combined petroleum ether when cooled gave 6.5 g of white crystal product which was separated by filtration. The oil residue, after removing excess petroleum ether under vacuum, crystallized. The crystals were separated by filtration and washed with petroleum ether to give 93 g of tan-colored material. Further work-up of the last petroleum ether filtrate gave 17 g additional crude product. Combined yield of crude tan product was 116.5 g (70%), m.p. 79°–84° C. A portion of the crude was recrystallized from 30/60 petroleum ether to give white crystalline product, m.p. 79°–84° C.

Analysis: Calculated for $C_{11}H_{10}Cl_3NO_2$: C,44.85; H,3.42; N,4.76. Found: C,45.10; H,3.45; N,4.87.

Preparation 5

3-(3,5-Dichlorophenoxy)-1-pyrrolidinecarbonyl Chloride

To a stirred solution of 200 ml of 2 molar phosgene in benzene under nitrogen gas was added dropwise over a 3 hr period, a solution of 115 g (0.358 mole) of 1-benzyl-3-(3,5-dichlorophenoxy)pyrrolidine in 100 ml of benzene. The resulting solution was concentrated on a rotary evaporator to give an oil. The oil was triturated three times with boiling 30/60 petroleum ether, decanting each time. The oil residue solidified on cooling. The solid was taken up in benzene and the solution filtered, charcoaled and filtered. Crystalline product was obtained by adding ligroin and cooling to 5° C. in the amount of 92.7 g (87.9%), m.p. 105°–107° C. A purer 3 g sample, m.p. 106°–108° C. was obtained from the petroleum ether on standing.

Analysis: Calculated for $C_{11}H_{10}NO_2Cl_3$: C44.85; H,3.42; N,4.76. Found: C,45.18; H,3.50; N,4.75.

Preparation 6

3-[(2,3-Dihydro-1H-inden-4-yl)oxy]-1-pyrrolidinecarbonyl Chloride

To a stirred solution of 6.9 g (0.07 mole) of phosgene in 100 ml of anhydrous benzene under nitrogen gas and cooled at 10° C. was added dropwise a solution of 18.13 g (0.062 mole) of 1-benzyl-3-(4-indanyloxy)pyrrolidine in 50 ml of dry benzene. After stirring for 18 hr, the slightly turbid reaction mixture was filtered through celite. The filtrate was washed with 50 ml of ice-water, dried over magnesium sulfate and concentrated on a rotary evaporator. The solid residue was triturated with boiling isopropyl ether. Fifteen grams of crude product was obtained by filtering the mixture. Recrystallization from a mixture of benzene and 30/60 petroleum ether gave 13.1 g of cream colored solid, m.p. 128°–129° C.

Analysis: Calculated for $C_{14}H_{16}NO_2Cl$: C,63.27; H,6.07; N,5.27. Found: C,63.47; H,6.13; N,5.27.

Preparation 7

3-[3-(1-Naphthalenyloxy)]-1-pyrrolidinecarbonyl Chloride

To a stirred solution of 30 ml of 2 molar phosgene (0.06 mole) in benzene under nitrogen gas was added dropwise a solution of 15.8 g (0.05 mole) of 1-benzyl-3-(1-naphthalenyloxy)pyrrolidine in 50 ml of benzene and 10.7 g (0.05 mole) of proton sponge (1,8-bis-(dimethylamino)naphthalene) in one portion. The reaction mixture was stirred at ambient temperature for 1.5 hr and filtered to remove a hydrochloric acid salt of the proton sponge. The filtrate was washed with ice-water followed by dilute hydrochloric acid, dried over magnesium sulfate and concentrated to a paste. The paste was triturated with boiling 30/60 petroleum ether to dissolve most of the paste. The undissolved solid (3.3 g of hydrochloric acid salt of the proton sponge) was separated by filtration. The filtrate was concentrated in vacuo to give an oil which crystallized from cold isopropyl ether, 8.9 g, m.p. 113°–115° C. White crystalline product, m.p. 116°–117° C. was obtained by recrystallization from diethyl ether.

Analysis: Calculated for $C_{15}H_{14}NO_2Cl$: C,65.34; H,5.12; N,5.08. Found: C,65.36; H,5.18; N,5.02.

Preparation 8

3-(3-Chlorophenoxy)-1-pyrrolidinecarbonyl Chloride

A benzene solution of 450 ml of 2M phosgene (0.9 mole) was cooled to 10° C. and while stirring, 210 g (0.81 mole) of 1-benzyl-3-(3-chlorophenoxy)pyrrolidine in 210 ml of tetrahydrofuran was added over a 3½ hr period. The reaction mixture was allowed to stir overnight and then filtered to remove the hydrochloric acid salt of unreacted starting material. The filtrate was evaporated to give a dark colored oil which was triturated with three 500 ml portions of 30/60 petroleum ether decanting off the petroleum ether each time from the oil residue. The petroleum ether layers were cooled and the oils which separated were combined to give 17 g of pure title product as an oil. After washing with more petroleum ether, the oil (203 g) residue contained about 17% benzyl chloride by NMR analysis. Yield of contained product in both portions was 88%.

Preparation 9

3-(2,6-Dichlorophenoxy)-1-pyrrolidinecarbonyl Chloride

To a solution of 170 ml of 2M phosgene (0.34 mole) stirred at 15° C. was added 109.2 g (0.34 mole) of 1-benzyl-3-(2,6-dichlorophenoxy)pyrrolidine in 300 ml of benzene. The color turned from yellow to deep amber. For convenience, the solution was allowed to stir for 72 hr, then concentrated to give a deep amber colored viscous oil. The oil was triturated with 1.6 liters of 30/60 petroleum ether. The petroleum ether wash was cooled to give 101.5 g of nearly pure title compound containing a trace of benzyl chloride. The yield was nearly quantitative.

Preparation 10

3-(2,3-Dichlorophenoxy)-1-pyrrolidinecarbonyl Chloride

To a solution of 200 ml of 2M phosgene in benzene, stirred under nitrogen gas, was added 96 g (0.3 mole) of 1-benzyl-3-(2,3-dichlorophenoxy)pyrrolidine in 300 ml of benzene. The reaction mixture was allowed to stir overnight and then concentrated to an oil. The oil was triturated with 30/60 petroleum ether to give an oil. Solid product, 89 g, was obtained containing a trace of benzyl chloride. The yield was nearly quantitative.

Preparation 11

3-(3-Bromophenoxy)-1-pyrrolidinecarbonyl Chloride

To a benzene solution of 5.05 g (0.051 mole) of phosgene in 50 ml of benzene at 10° C. under nitrogen gas was added dropwise 15.5 g (0.047 mole) of 1-benzyl-3-(3-bromophenoxy)pyrrolidine in 50 ml of dry benzene. The reaction mixture was stirred for 6 hr, diluted with ice-water mixture. The benzene layer which developed was separated and dried over magnesium sulfate and concentrated in vacuo to give 27 g of oil. The oil was triturated with hot 30/60 petroleum ether and the mixture stirred overnight. The petroleum layer was decanted and the oil again treated with fresh petroleum ether. The oil was again separated to give 20 g of oil crude product.

Preparation 12

3-Phenoxy-1-pyrrolidinecarbonyl Chloride

To a solution of 9.5 g (0.097 mole) of phosgene in 200 ml of methylene chloride under nitrogen gas was added dropwise with stirring, 30.2 g (0.88 mole) of 1-benzyl-3-phenoxypyrrolidine in 100 ml of methylene chloride over a 45 minute period. The reaction mixture was stirred additionally for 20 minutes. The reaction mixture was concentrated in vacuo to give 31.9 g of oil. The oil was triturated with boiling 30/60 petroleum ether and the mixture was cooled. The ether layer was decanted off and the trituration in petroleum ether procedure was repeated 3 times. The oil contained a trace of benzyl chloride as indicated by thin-layer chromatography.

Preparation 13

3-[(2,3-Dihydro-1H-inden-5-yl]-1-pyrrolidinecarbonyl Chloride

Following the procedure of Preparation 6, 1-benzyl-3-(5-indanyloxy)pyrrolidine is reacted with phosgene and isolated to give the title compound.

Preparation 14

3-[3-(2-Naphthalenyloxy)]-1-pyrrolidinecarbonyl Chloride

Following the procedure of Preparation 7, 1-benzyl-3-(2-naphthalenyloxy)pyrrolidine is reacted with phosgene and isolated to give the title compound.

Preparation 15 (a-d)

When in the procedure of Preparation 1, the following are substituted for 1-benzyl-3-(3-methylphenoxy)-pyrrolidine:
1-benzyl-3-(3-ethylphenoxy)pyrrolidine,
1-benzyl-3-[3-(trifluoromethyl)phenoxy]pyrrolidine,
1-benzyl-3-[4-(trifluoromethyl)phenoxy]pyrrolidine, and,
1-benzyl-3-(4-chlorophenoxy)pyrrolidine,
there are obtained:
 (a) 3-(3-ethylphenoxy)-1-pyrrolidinecarbonyl chloride,
 (b) 3-[3-(trifluoromethyl)phenoxy]-1-pyrrolidinecarbonyl chloride,
 (c) 3-[4-(trifluoromethyl)phenoxy]-1-pyrrolidinecarbonyl chloride, and,
 (d) 3-(4-chlorophenoxy)-1-pyrrolidinecarbonyl chloride.

Preparation 16

3-(3,4-Dichlorophenoxy)-1-piperidinecarbonyl Chloride

To a stirred solution of 8 g (0.085 mole) of phosgene in 100 ml of methylene chloride at 5° C. under nitrogen gas was added slowly a solution of 27.1 g (0.081 mole) of 1-benzyl-3-(3,4-dichlorophenoxy)piperidine in 50 ml of methylene chloride. The reaction mixture was allowed to warm to room temperature over a 2 hr period and then concentrated to a light oil. The oil was triturated with hexane. Starting material, 1.6 g as fine white precipitate, was separated by filtration. The oil was triturated four more times with hexane to remove benzyl chloride. The remaining oil was taken up in 200 ml of benzene and 50 ml of pyridine was added. The mixture was allowed to stir overnight. Some quaternary benzyl chloride salt precipitated and was discarded. The title compound in solution was used in Example 12.

Preparation 17

4-(3,4-Dichlorophenoxy)-1-piperidinecarbonyl Chloride

To a stirred solution of 16 g (0.16 mole) of phosgene in 200 ml of methylene chloride at 15° C. under nitrogen gas was added dropwise a solution of 47.2 g (0.14 mole) of 1-benzyl-4-(3,4-dichlorophenoxy)piperidine in 100 ml of methylene chloride. The addition was complete within 1 hr and stirring was continued for an additional hour. The mixture was concentrated on a rotary evaporator to give a light oil. The oil was dissolved in isopropyl ether and the mixture filtered to remove a small amount of insoluble material. The filtrate was washed with 50 ml of water, dried over magnesium sulfate, filtered and concentrated in vacuo to an oil. The oil was triturated four times with 100 ml of hexane decanting off the hexane each time after cooling. The oil residue, 37 g (86%), was treated with 10 ml of triethylamine to quaternize (precipitate) any excess benzyl chloride.

Preparation 18

3-(3-Methylphenoxy)-1-pyrrolidinecarbothioyl Chloride

Utilizing the procedure of Preparation 1 but substituting thiophosgene for phosgene, 1-benzyl-3-(3-methylphenoxy)pyrrolidine is converted to the title compound.

Preparation 19

Utilizing procedures selected from techniques of Preparations 1 to 12 and 16 and 17, the following are reacted with thiophosgene:
1-benzyl-3-(2-methoxyphenoxy)pyrrolidine,
1-benzyl-3-(3-chloro-4-fluorophenoxy)pyrrolidine,
1-benzyl-3-(3,4-dichlorophenoxy)pyrrolidine,
1-benzyl-3-(3,5-dichlorophenoxy)pyrrolidine,
1-benzyl-3-(4-indanyloxy)pyrrolidine,
1-benzyl-3-(1-naphthalenyloxy)pyrrolidine,
1-benzyl-3-(3-chlorophenoxy)pyrrolidine,
1-benzyl-3-(2,6-dichlorophenoxy)pyrrolidine,
1-benzyl-3-(2,3-dichlorophenoxy)pyrrolidine,
1-benzyl-3-(3-bromophenoxy)pyrrolidine,
1-benzyl-3-phenoxypyrrolidine,
1-benzyl-3-(5-indanyloxy)pyrrolidine,
1-benzyl-3-(2-naphthalenyloxy)pyrrolidine,
1-benzyl-3-(3-ethylphenoxy)pyrrolidine,
1-benzyl-3-[3-(trifluoromethyl)phenoxy]pyrrolidine,
1-benzyl-3-[4-(trifluoromethyl)phenoxy]pyrrolidine,
1-benzyl-3-(4-chlorophenoxy)pyrrolidine,
1-benzyl-3-(3,4-dichlorophenoxy)piperidine, and
1-benzyl-4-(3,4-dichlorophenoxy)piperidine,
to give the following:
3-(2-methoxyphenoxy)-1-pyrrolidinecarbothioyl chloride,
3-(3-chloro-4-fluorophenoxy)-1-pyrrolidinecarbothioyl chloride,
3-(3,4-dichlorophenoxy)-1-pyrrolidinecarbothioyl chloride,
3-(3,5-dichlorophenoxy)-1-pyrrolidinecarbothioyl chloride,
3-(4-indanyloxy)-1-pyrrolidinecarbothioyl chloride,
3-(1-naphthalenyloxy)-1-pyrrolidinecarbothioyl chloride,
3-(3-chlorophenoxy)-1-pyrrolidinecarbothioyl chloride,
3-(2,6-dichlorophenoxy)-1-pyrrolidinecarbothioyl chloride,
3-(2,3-dichlorophenoxy)-1-pyrrolidinecarbothioyl chloride,
3-(3-bromophenoxy)-1-pyrrolidinecarbothioyl chloride,
3-phenoxy-1-pyrrolidinecarbothioyl chloride,
3-(5-indanyloxy)-1-pyrrolidinecarbothioyl chloride,
3-(2-naphthalenyloxy)-1-pyrrolidinecarbothioyl chloride,
3-(3-ethylphenoxy)-1-pyrrolidinecarbothionyl chloride,
3-[3-(trifluoromethyl)phenoxy]-1-pyrrolidinecarbothioyl chloride,
3-[4-(trifluoromethyl)phenoxy]-1-pyrrolidinecarbothioyl chloride,
3-(4-chlorophenoxy)-1-pyrrolidinecarbothioyl chloride,
3-(3,4-dichlorophenoxy)-1-pyrrolidinecarbothioyl chloride, and 4-(3,4-dichlorophenoxy)-1-piperidinecarbothioyl chloride.

Preparation 20

When in the procedure of Preparation 1, the following are substituted for 1-benzyl-3-(3-methylphenoxy)pyrrolidine:
1-benzyl-3-(2-methylphenoxy)pyrrolidine,
1-benzyl-3-(2-ethoxyphenoxy)pyrrolidine,
1-benzyl-3-(4-methoxyphenoxy)pyrrolidine,
1-benzyl-3-(4-fluorophenoxy)pyrrolidine,
1-benzyl-3-(3,5-dimethylphenoxy)pyrrolidine,
1-benzyl-3-(3-methoxyphenoxy)pyrrolidine,
1-benzyl-3-(4-chlorophenoxy)pyrrolidine,
1-benzyl-3-(4-bromophenoxy)pyrrolidine, and
1-benzyl-3-(3,5-dimethoxyphenoxy)pyrrolidine,
there are obtained:
  (a) 3-(2-methylphenoxy)-1-pyrrolidinecarbonyl chloride,
  (b) 3-(2-ethoxyphenoxy)-1-pyrrolidinecarbonyl chloride,
  (c) 3-(4-methoxyphenoxy)-1-pyrrolidinecarbonyl chloride,
  (d) 3-(4-fluorophenoxy)-1-pyrrolidinecarbonyl chloride,
  (e) 3-(3,5-dimethylphenoxy)-1-pyrrolidinecarbonyl chloride,
  (f) 3-(3-methoxyphenoxy)-1-pyrrolidinecarbonyl chloride,
  (g) 3-(4-chlorophenoxy)-1-pyrrolidinecarbonyl chloride,
  (h) 3-(4-bromophenoxy)-1-pyrrolidinecarbonyl chloride, and
  (i) 3-(3,5-dimethoxyphenoxy)-1-pyrrolidinecarbonyl chloride.

Preparaton 21

When in the procedure of Preparation 1, the following are substituted for 1-benzyl-3-(3-methylphenoxy)pyrrolidine:
1-benzyl-4-(4-bromophenoxy)piperidine,
1-benzyl-4L-phenoxypiperidine,
1-benzyl-4-(3-trifluoromethylphenoxy)piperidine, and
1-benzyl-4-(4-trifluoromethylphenoxy)piperidine,
there are obtained:
4-(4-bromophenoxy)-1-piperidinecarbonyl chloride,
4-(phenoxy)-1-piperidinecarbonyl chloride,
4-(3-trifluoromethylphenoxy)-1-piperidinecarbonyl chloride, and
4-(4-trifluoromethylphenoxy)-1-piperidinecarbonyl chloride.

Preparation 22

3-(3,5-Dichlorophenoxy)pyrrolidine Hydrochloride

To a stirred solution of 36 g (0.12 mole) of 3-(3,5-dichlorophenoxy)-1-pyrrolidinecarbonyl chloride in 20 ml of methanol was slowly added 150 ml of 6N sulfuric acid. The resulting turbid solution was stirred at 70° C. for 2 hr. The resulting clear solution was cooled by adding ice and extracted with two 20 ml portions of benzene. The acid layer was made basic by pouring it into a stirred slurry of 160 ml of 6N sodium hydroxide and ice. The resulting milky mixture was extracted with three 100 ml portions of benzene. These latter benzene extracts were combined, washed with water, dried over magnesium sulfate and concentrated to give 31 g of deep amber oil. The oil was dissolved in isopropyl alcohol and reacted with ethereal hydrogen chloride. The resulting tan solid, 22 g (68%) was recrystallized from isopropyl alcohol-isopropyl ether using activated charcoal to decolorize. Silver-colored plate-like crystals were obtained, m.p. 144°–145° C.

Analysis: Calculated for $C_{10}H_{12}NOCl_3$: C,44.72; H,4.50; N,5.22. Found: C,44.56; H,4.53; N,5.19.

Preparation 23

3-(3,4-Dichlorophenoxy)-1-pyrrolidinecarbothioyl Chloride 3-(3,5-Dichlorophenoxy)pyrrolidine hydrochloride in a solvent mixture with excess tri-ethylamine is reacted with thiophosgene to give the title compound. The triethylamine hydrochloride by-product is removed by filtration and the product isolated by evaporating off excess solvent and triethylamine.

The following examples are provided merely by way of illustration and are not to be construed as being limiting in nature.

EXAMPLE 1

3-(3-Chlorophenoxy)-N-[2-(dimethylamino)ethyl]-1-pyrrolidinecarboxamide ethanedioate [1:1]

A stirred solution of 13 g (0.05 mol) 1-chlorocarbonyl-3-(3-chlorophenoxy)pyrrolidine in 100 ml of chloroform was treated with 8.8 g (0.1 mol) of N,N-dimethyl-ethylenediamine dropwise and allowed to stir for 18 hours. The mixture was transferred to a separatory funnel and washed with 2×50 ml of water, dried over magnesium sulfate and concentrated to a dark oil (14 g). The oil was dissolved in 50 ml of isopropanol and 2.5 g of oxalic acid-dihydrate in 50 ml of isopropanol was added. Isopropyl ether was added until milky, cleared by heating and allowed to crystallize overnight to yield 7.5 g (47%), m.p. 78.5°–83° C.

Analysis: Calculated for $C_{15}H_{22}ClN_3O_2.C_2H_2O_4$: C,50.81; H,6.02; N,10.46. Found: C,59.98; H,5.96; N,10.14.

EXAMPLE 2

3-(2,6-Dichlorophenoxy)-N-(3-dimethylamino)propyl)-1-pyrrolidinecarboxamide Compound with Cyclohexylaminosulfonic Acid A mixture of 11.8 g (0.04 mole) of 3-(2,6-dichlorophenoxy)-1-pyrrolidinecarbonyl chloride, 5.5 g of potassium carbonate and 50 ml of chloroform was stirred and cooled to 0°–50° C. by the addition of ice. This mixture was treated with 4.08 g (0.04 mole) of N,N-dimethyl-1,3-propylenediamine in one portion and stirred for 20 hours. The chloroform phase was separated, dried over magnesium sulfate and concentrated to a yellow oil, 15.2 g, in vacuo. This crude product was treated with 125 g of Florisol in chloroform slurry and filtered. The Florisil residue was washed with chloroform, then acetone, and lastly methanol. The acetone wash gave 4 g of yellow oil and the methanol wash gave 5 g of the same yellow oil by TLC analysis, 2% methanol/chloroform. A portion was converted to the hexamate salt in isopropanol and the volume reduced under nitrogen gas until milky; after 3 weeks, crystallization took place. The remaining oil was converted to the hexamate salt in like manner. The salts were combined and recrystallized from isopropyl alcohol/isopropyl ether (50/50), to give 7.5 g of white crystals; m.p. 146°–147° C.

Analysis: Calculated for $C_{16}H_{23}N_3O_2Cl_2 \cdot C_6H_{11}NHSO_3H$: C,48.98; H,6.73; N,10.38. Found: C,48.99; H,6.77; N,10.34.

EXAMPLE 3

3-(2,3-Dichlorophenoxy)-N-(2-dimethylaminoethyl)-1-pyrrolidinecarboxamide

A solution 11.8 g (0.04 mole) of 3-(2,3-dichlorophenoxy)-1-pyrrolidinecarbonyl chloride in 50 ml of chloroform was stirred at 5° C. in an ice bath while the following were added in order: 25 g of ice, 5.52 g of potassium carbonate and 3.87 g (0.044 mole) of N,N-dimethylethylenediamine. The resulting mixture was stirred for 20 hours and worked up by adding additional water followed by separation of the organic phase. The chloroform solution was dried over magnesium sulfate, filtered and concentrated in vacuo to a dark amber oil, 14 g, which solidified on standing. TLC analysis (10% methanol/chloroform) showed 3 spots; therefore, the crude product was chromatographed on 50 g of Fluorisil. Elution with chloroform gave a dark forerun which was discarded, the main portion was collected and rechromatographed through a 50 g Florisil column. The column was washed with 200 ml of methanol and the 2 fractions (chloroform and methanol) were combined before concentrating on a rotary evaporator to give a light amber oil which solidified. Recrystallization from isopropyl ether gave a beige crystalline product; 4.5 g (34%), m.p. 94°-95° C.

Analysis: Calculated for $C_{15}H_{21}N_3O_2Cl_2$: C,52.03; H,6.11; N,12.14. Found: C,52.21; H,6.14; N,12.05.

EXAMPLE 4

3-(2,3-Dichlorophenoxy)-N-[3-(dimethylamino)-propyl]-1-pyrrolidinecarboxamide Hydrochloride, Dihydrate A solution 11.8 g (0.04 mole) of 3-(2,3-dichlorophenoxy)-1-pyrrolidinecarbonyl chloride in 50 ml of chloroform was stirred at 5° C. in an ice bath while the following were added in order: 25 g of ice; 5.52 g of potassium carbonate; and 4.05 g (0.044 mole) of N,N-dimethylpropylene-1,3-diamine. The resulting mixture was stirred for 20 hrs at room temperature, then diluted with water and the organic layer separated. The organic phase was washed with water, dried over magnesium sulfate, filtered, and concentrated in vacuo to a dark amber oil, 15.2 g. The oil was converted to the hydrochloric acid salt with ethereal hydrogen chloride and trituration first with ethyl ether, then with acetone to give a grayish product, 17 g, which proved to be hygroscopic on standing. Two recrystallizations, after treating with charcoal, from isopropyl alcohol/isopropyl ether gave a gray powder: 7.6 g (49%), m.p. 145°-148° C.(degasses). The solid material, the mother liquor and the washes were all combined and treated with 3N sodium hydroxide and following work-up gave 7 g of free base. A TLC analysis showed 2 spots. Thus, the crude product was chromatographed on 200 g of Florisil. Elution with benzene with an acetone gradient gave first the less polar impurity and finally with pure acetone the desired product. The acetone fractions were concentrated to give 3.5 g of pale yellow oil. The oil was converted to the HCl salt and recrystallized from isopropyl alcohol/isopropyl ether to give a white granular solid; 4 g, m.p. 130°-142° C.; after drying at 78° C. for 64 hours under high vacuum, m.p. 145°-148° C. (degasses).

Analysis: Calculated for $C_{16}H_{23}N_3O_2Cl_2 \cdot HCl \cdot 2H_2O$: C,44.41; H,6.52; N,9.71. Found: C,44.08; H,5.80; N,9.55.

EXAMPLE 5

3-(3-Chlorophenoxy)-N-[3-(dimethylamino)propyl]-1-pyrrolidinecarboxamide

A solution, 13 g (0.05 mole) of 3-(3-chlorophenoxy)-1-pyrrolidinecarbonyl chloride in 100 ml of chloroform was stirred at 0° C. for 5 min. Then, the following were added in order: 25 g of ice, 12.8 g of sodium carbonate; and 5.62 g (0.055 mole) of N,N-dimethyl-1,3-propanediamine. The resulting mixture was allowed to come to room temperature and stirred for 72 hours. At this time the reaction mixture was diluted with excess water and the organic phase separated. The chloroform solution was washed with water and extracted with 50 ml of 3N hydrochloric acid. The chloroform portion was washed with 2×25 ml of water. The hydrochloric acid portion was combined with the last 2 washes and the pH adjusted to neutral with 3N sodium hydroxide. The resulting solution was extracted with 3×30 ml of chloroform and the chloroform extracts were combined, dried over magnesium sulfate and concentrated to a dark oil, 13.2 g. All of the samples were converted to the free base, charcoaled, and chromatographed on 25 g of silica gel. Elution with chloroform gave after concentrating a dark orange oil. Trituration of this oil with ethyl ether and concentration of the triturates gave 7 g of a pale yellow viscous oil. This oil was pumped under high vacuum for 24 hours. The oil upon standing crystallized and was recrystallized from ethyl ether/30-60 petroleum ether to give 3.2 g of fine white crystals; m.p. 60°-61° C.

Analysis: Calculated for $C_{16}H_{24}N_3O_2Cl_1$: C,58.98; H,7.42; N,12.90. Found: C,58.99; H,7.48; N,12.71.

EXAMPLE 6

3-(3,5-Dichlorophenoxy)-N-[2-(dimethylamino)ethyl]-1-pyrrolidinecarboxamide, Ethanedioate (1:1)

A stirred solution of 7.4 g (0.025 mole) 3-(3,5-dichlorophenoxy)-1-pyrrolidinecarbonyl chloride in 75 ml of tetrahydrofuran was treated with 3.45 g (0.025 mole) of potassium carbonate and 20 g of ice. This mixture was stirred for 5 minutes then treated with 2.4 g (0.03 mole) of N,N-dimethylethylenediamine and stirred at ambient temperature overnight. Enough sodium chloride was added to the mixture to give a phase separation (tetrahydrofuran and aqueous). The phases were separated and the tetrahydrofuran portion dried over magnesium sulfate and concentrated in vacuo to give 9 g of a pale amber oil. The sample was converted to the oxalate salt which gave after recrystallization from isopropyl alcohol/isopropyl ether ca. 2 g of crystalline product, dried at 82° C. under reduced pressure, m.p. 115°-120° C. The product was contaminated with isopropyl.

Analysis: Calculated for $C_{15}H_{21}N_3O_2Cl_2 \cdot C_2H_2O_4$: C,46.80; H,5.31; N,9.63. Found: C,47.02; H,5.52; N,9.20.

A later preparation using acetone as recrystallization solvent gave title compound free of solvent, m.p. 166°-168° C.

Analysis: Found: C,46.79; H,5.34; N,9.69.

EXAMPLE 7

3-(3,5-Dichlorophenoxy)-N-[2-(dimethylamino)ethyl-1]-pyrrolidinecarboxamide

A stirred solution of 113 g (0.384 mole) of 3-(3,5-dichlorophenoxy)-1-pyrrolidinecarbonyl chloride in 1 liter of tetrahydrofuran was treated with 67 g (0.77 mole) of N,N-dimethylethylenediamine all at once and allowed to stir overnight at ambient temperature. The reaction mixture was diluted with 500 ml of isopropyl ether and the solid material removed by filtration. The filtrate was concentrated in vacuo to give 156 g of dark oil which was dissolved in 600 ml of benzene. The solution was washed with 4×200 ml of water, dried over magnesium sulfate, and the solvent removed in vacuo to give 120 g of oil. Trituration with hexane gave 107 g of gray crystalline product which was recrystallized from isopropyl ether/hexane to give 97.5 g of white crystalline powder, m.p. 92–93.5° C.

Analysis: Calculated for $C_{15}H_{21}N_3O_2Cl_2$: C,52.03; H,6.11; N,12.14. Found: C,52.17; H,6.15; N,12.11.

EXAMPLE 8

3-(3,5-Dichlorophenoxyl)-N-[3-(dimethylamino)-propyl]-1-pyrrolidinecarboxamide, Ethanedioate [1:1]

A solution of 7.5 g (0.025 mole) of 3-(3,5-dichlorophenoxy)-1-pyrrolidinecarbonyl chloride in 50 ml of methylenechloride was treated with the dropwise addition of 3 g (0.03 mole) of N,N-dimethyl-1,3-propylenediamine. After stirring for 5 minutes at room temperature a fine crystalline precipitate separated. After 20 minutes TLC (10% methanol/benzene on silica gel) showed no carbamoyl chloride. The mixture was diluted with 50 ml of ethyl ether and cooled in the refrigerator overnight. Filtration gave only about 1 g of material identified by mass spectra as the hydrochloride of starting diamine. The filtrate was concentrated in vacuo to a yellow oil, and the oil was dissolved in isopropyl alcohol and treated with ethereal hydrogen chloride to give a milky oil which solidified and was removed by trituration with acetone. Filtration yielded 9.1 g of crude product. A mass spectrum (EI) had the expected parent ion at 359 with 2 chlorides. The product which was hygroscopic was converted to the free base and the fumarate salt formed. It, too, was hygroscopic; likewise, the oxalate salt appeared hygroscopic. The hygroscopic salts form crystalline hydrates but cannot be recrystallized. The free base, 6 g, was chromatographed on a 120 g alumina column and eluted with chloroform and gave the product in one 50 ml fraction after discarding the first 10 ml. Concentration in vacuo gave 5.8 g of yellow oil. The oil was converted to the oxalate salt in isopropyl alcohol and treated with isopropyl ether which first gave an amorphous gel, then the product crystallized. All the solids were redissolved and additional isopropyl ether was added. When the amorphous gel separated it was removed by filtration and the hot solution treated with charcoal. The charcoal was removed and on cooling, a crystalline product separated which upon isolation appeared to be hygroscopic. It was dried in a drying pistol under high vacuum at 98° C. for 3 hours to yield 3 g, m.p. 117°–118° C.

Analysis: Calculated for $C_{16}H_{23}Cl_2N_3O_2.C_2H_2O_4$: C,48.01; H,5.60; N,9.33. Found C,48.20; H,5.68; N,9.20.

EXAMPLE 9

N-[2-(Dimethylamino)ethyl]-3-phenoxy-1-pyrrolidinecarboxamide

A stirred solution of 0.088 mole of crude 3-phenoxy-1-pyrrolidinecarbonyl chloride in 100 ml of tetrahydrofuran was cooled to 0° C., treated with 7 g (0.088 mole) of pyridine (to remove any benzyl chloride contaminant), warmed to ambient temperature (1 hr.) and treated with 15.5 g (0.176 mole) of N,N-dimethylethylenediamine at a rapid drop rate. The reaction was slightly exothermic and after 2 hours, the mixture was filtered to remove a fine silvery precipitate (hydrochloride of the diamine) and concentrated in vacuo to a dark oil. The oil was partitioned between isopropyl ether and water, the isopropyl ether phase separated and the aqueous portion extracted with 100 ml of isopropyl ether. The isopropyl ether extracts were combined and concentrated in vacuo to give an amber oil, 5 g. The aqueous phase was extracted with 3×50 ml of benzene, the extracts combined, washed with 20 ml of water, dried over magnesium sulfate and concentrated in vacuo to a dark oil, 12 g. This residue partially crystallized overnight and was recrystallized 2 times with charcoal treatment, first from isopropyl ether/ligroin, then from isopropyl ether (cooled in a refrigerator) to give 4.1 g of white crystalline product which after drying at 64° C. under reduced pressure for 18 hours weighed 3.9 g, m.p. 72°–73° C. The residue from the original isopropyl extracts (5 g) was combined with the filtrate from above and upon reworking, gave an additional 4.3 g of product, m.p. 71°–73° C. The fraction with m.p. 72°–73° C. was submitted for elemental analysis and testing.

Analysis: Calculated for $C_{15}H_{23}N_3O_2$: C,64.96; H,8.36; N,15.15. Found C,65.01; H,8.36; N,15.16.

EXAMPLE 10

3-(3-Chlorophenoxy)-N-[2-(dimethylamino)ethyl]-N-methyl-1-pyrrolidinecarboxamide Ethanediote The dimsyl anion, formed by heating and stirring a mixture of 2.0 g (0.04 mole) of sodium hydride (50% in mineral oil) and 100 ml of dimethyl sulfoxide under nitrogen at 80° C. until the evolution of hydrogen eased, was cooled to 15° C., treated with 10 g (0.04 mole) of 3-(3-chlorophenoxy-N-methyl-1-pyrrolidinecarboxamide added in one portion and the mixture stirred 1 hour. It was treated dropwise with 7.2 g (0.05 mole) of N,N-dimethylaminoethyl chloride hydrochloride (converted to the free base) in methylene chloride. The mixture was stirred for 18 hours at ambient temperature, diluted with 200 ml of water, and extracted with 5×50 ml of benzene. The benzene extracts were combined, washed with 20 ml of water, and extracted with 4×50 ml of 3N hydrochloric acid. The acid extracts were made basic with 6N sodium hydroxide and extracted with 3×50 ml of methylene chloride. The combined extracts were washed with 20 ml of water, dried over magnesium sulfate and concentrated in vacuo to give a dark oil, 18 g. The oil was chromatographed on a 400 g alumina column and eluted with ethyl acetate to give 6 fractions. The first and last contained no product and were discarded. The others were combined and concentrated to give 9 g of oil. The residue was treated with 2.7 g oxalic acid in 100 ml of 2-propanol. The mixture was heated to dissolve the solids, filtered and cooled to ambient temperature over several days. The crystallized product was collected by filtration to give 2.5 g of white granular product, m.p. 139°–140° C.

Analysis: Calculated for $C_{16}H_{24}ClN_3O_2.C_2H_2O_4$: C,51.99; H,6.30; N,10.10. Found: C,51.92; H,6.28; N,10.14.

EXAMPLE 11

3-(3,4-Dichlorophenoxy)-N-[2-(dimethylamino)ethyl]-1-pyrrolidine Carboxamide Hydrochloride A stirred solution of 17.7 g (0.06 mole) of 3-(3,4-dichlorophenoxy)-1-pyrrolidinecarboxamide in 170 ml of tetrahydrofuran was treated by the rapid addition of 10.6 g (0.12 mole) of N,N-dimethylethylenediamine. The reaction was slightly exothermic and the mixture was stirred at ambient temperature over the weekend. Filtration removed some precipitated diamine hydrochloride, and the filtrate was concentrated in vacuo to give an oil, 23 g. The oil was treated with ethereal hydrogen chloride to give a granular solid which was recrystallized twice from acetone to give 4.6 g of pale green product, m.p. 143°–145° C.

Analysis: Calculated for $C_{15}H_{21}Cl_2N_3O_3.HCl$: C,47.08; H,5.79 N,10.98. Found: C,46.51; H,5.78 N,10.88.

EXAMPLE 12

3-(3,4-Dichlorophenoxy)-N-[2-(dimethylamino)ethyl]-1-piperidinecarboxamide Ethanedioate A solution of (ca. 0.07 mole) of crude 3-(3,4-dichlorophenoxy)-1-piperidinecarbonyl chloride in 200 ml of benzene was stirred under nitrogen while 12.4 g (0.14 mole) of N,N-dimethylethylenediamine was added all at once. After stirring at ambient temperature for 18 hours, a fine gelatinous precipitate was removed by filtration and the filtrate washed with water, dried over magnesium sulfate and concentrated in vacuo to give a dark oil (contains some solvent). TLC (10% methanol/benzene; silica gel) showed one major spot. The oil was treated with 8.8 g (0.07 mole) of oxalic acid dihydrate and allowed to sit for a few days. The solid was suspended in acetone and filtration gave 20 g of crude tan oxalate salt. After filtration, the crude solids were recrystallized from 2-propanol/isopropyl ether. The filtered product was still wet with solvent and gave a hard cake after air drying. The solid was broken up and sieved to give an amorphous-like powder, dried at reduced pressure for a few days, 13.53 g, m.p. 135°–138° C. (degasses).

Analysis: Calculated for $C_{16}H_{23}N_3O_2Cl_2.C_2H_2O_4$: C,48.01; H,5.60; N,9.33. Found C,47.93; H,5.59; N,9.47.

EXAMPLE 13

4-(3,4-Dichlorophenoxy)-N-[2-(dimethylamino)ethyl]-N-methyl-1-piperidinecarboxyamide Hydrochloride A stirred solution of 18.5 g (0.06 mole) of 4-(3,4-dichlorophenoxy)-1-piperidinecarbonyl chloride in 150 ml of tetrahydrofuran was treated all at once with 9.2 g (0.09 mole) of N,N',N'-trimethylethylenediamine. The reaction was exothermic and a solid precipitated (HCl salt of the starting diamine). After 4 hours, the mixture was filtered and the filtrate concentrated in vacuo. The 29 g of viscous oil was dissolved in methylene chloride, washed with 3N sodium hydroxide, and concentrated again to give 23 g of oil. The TLC (20% ethyl acetate/methylene chloride; alumina) of this oil showed 1 major spot and 2 minor spots. It was chromatographed on a 400 g alumina column by eluting first with methylene chloride then with a 1–5% ethyl acetate/methylene chloride gradient. The effluent, at 5% ethyl acetate/methylene chloride, was collected in six fractions. Five of these fractions contained product and were combined and concentrated in vacuo to give 8 g of pale yellow oil. The oil was treated with ethereal-HCl and the resulting gum crystallized when triturated with fresh ethyl ether. Recrystallization from acetone/isopropyl ether gave 7.2 g of fine white crystals, m.p. 183°–184° C.

Analysis: Calculated for $C_{17}H_{25}N_3O_2Cl_2.HCl$: C,49.71; H,6.38; N,10.23. Found C,49.61; H,6.42; N,10.34.

EXAMPLE 14

3-(3-Chlorophenoxy)-N-[3-(diethylamino)propyl]-1-pyrrolidinecarboxamide

A stirred solution, 13 g (0.05 mole) of 3-(3-chlorophenoxy)-1-pyrrolidinecarbonyl chloride in 100 ml of chloroform was treated with 25 mg of ice and 12.8 g of sodium carbonate after 5 min. This mixture was treated with 7.15 g (0.055 mole) of N,N-diethyl-1,3-propanediamine dropwise and allowed to stir for 78 hours. The reaction mixture was transferred to a separatory funnel and enough water was added to form two distinct phases. The organic phase (chloroform) was separated and washed with 50 ml of water; the organic portion was extracted with 50 ml of 3N hydrochloric acid, separated and washed with 2×25 ml of water. All the aqueous portions were combined and the pH adjusted to neutral with 3N sodium hydroxide and extracted with 4×30 ml of chloroform. The extract was combined, washed with water, dried over magnesium sulfate and concentrated on a rotary vacuum to a pale yellow oil (12 g). The oil was dissolved in chloroform, treated with 1.5 g of charcoal and filtered hot. This was then slurried with 25 g of silica gel and filtered. The chloroform was discarded and the silica gel washed with methanol to give, after concentrating, 4 g of pale yellow oil. This was dissolved in ethyl ether and filtered through celite.

Analysis: Calculated for $C_{16}H_{28}ClN_3O_2$: C,61.09; H,7.98; N,11.87. Found: C,60.96; H,7.84; N,11.45.

EXAMPLE 15

3-(3-Dichlorophenoxy-N-[2-(dimethylamino)ethyl]-N-methyl-1-pyrrolidinecarboxamide ethanedioate A stirred solution of 10.2 g (0.035 mole) of 3-(3,5-dichlorophenoxy)-1-pyrrolidinecarbonyl chloride in 100 ml of tetrahydrofuran was treated all at once with 7.1 g (0.07 mole) of N,N,N'-trimethylethylenediamine, stirred overnight at ambient temperature, filtered and concentrated in vacuo to give 12.8 g of brown oil. The oil was dissolved in acetone and treated with oxalic acid. The resulting solution was diluted with isopropyl ether until an oil separated. After 1 month the oil had not crystallized. NMR and mass spectra showed that the oil was the expected product. The oil was converted to the free base (11 g) and chromatographed on a 300 g alumina column by eluting with a 1–50% ethyl acetate/methylene chloride gradient. The tenth fraction collected was the purest and it was converted to the oxalate salt which crystallized. The purest fractions were combined and converted to the oxalate salt. The salts were combined and recrystallized from acetone/isopropyl ether to give 5.2 g of white powder, m.p. 168°–169° C.

Analysis: Calculated for $C_{16}H_{23}N_3O_2Cl \cdot C_2H_2O_4$: C,48.01; H,5.59; N,9.33. Found C,47.85; H,5.66; N,9.24.

EXAMPLE 16

3-(3-Chlorophenoxy)-N-[2-(dimethylamino)ethyl]-N-ethyl-1-pyrrolidinecarboxamide Ethanedioate A stirred solution of 13 g (0.05 mole) of 3-(3-chlorophenoxy)-1-pyrrolidinecarbonyl chloride and 10 g (0.1 mole) of triethylamine in 75 ml of tetrahydrofuran was treated all at once with 5.8 g (0.05 mole) of N,N-dimethyl-N'-ethylethylenediamine and stirred at ambient temperature for 18 hours. The mixture was diluted with 30 ml of water, made basic with 3N sodium hydroxide and extracted with 4×25 ml of 150 propyl ether. The combined extracts were washed with water, dried over magnesium sulfate, filtered and concentrated in vacuo to give a crude oil. The oil was chromatographed on a 400 g alumina column by eluting with a 0–100% methanol/methylene chloride gradient. The effluent was collected in 19 fractions. Fractions 11–13 were combined to give 5.2 g of oil and fractions 14–17 were combined to give additional oil. The residue oils were converted to the oxalate salts separately. The oxalate salts were combined and recrystallized from acetone/isopropyl ether to give a hygroscopic gel-like solid. After repeated recrystallization to remove the gel-like material, 0.8 g of white powder was obtained, m.p. 126°–128° C.

Analysis: Calculated for $C_{17}H_{26}N_3O_2Cl_1 \cdot C_2H_2O_4$: C,53.08; H,6.57; N,9.77. Found C,53.06; H,6.59; N,9.96.

EXAMPLE 17

3-(3,5-Dichlorophenoxy)-N-[2-(diethylamino)ethyl]-N-ethyl-1-pyrrolidinecarboxamide A stirred solution of 7 g (0.024 mole) of 3-(3,5-dichlorophenoxy)-1-pyrrolidinecarbonyl chloride in 70 ml of tetrahydrofuran was treated with 7 g (0.05 mole) of N,N,N'-triethylethylenediamine (slight exothermic) and stirred at ambient temperature overnight. The mixture filtered to remove a small amount of precipitate. The filtrate was diluted with 200 ml of ice water, extracted with 3×100 ml of benzene and the combined extracts washed with water, dried over magnesium sulfate and concentrated in vacuo to give a pale brown oil, 8.24 g. The oil was dissolved in acetone, treated with 1.9 g of oxalic acid and heated until dissolved. A fine amorphous gel was removed by filtration and the filtrate diluted with isopropyl ether until cloudy. The salt was allowed to precipitate overnight. After 2 weeks the oil which separated from the acetone/isopropyl ether failed to crystallize. The solvents were removed by decantation and the residual oil converted back to the free base. The free base in methylene chloride was treated with 200 g of florisil and diluted with enough methylene chloride to give a stirrable slurry. After 30 minutes the slurry was filtered and the florisil washed with 2 volumes of methylene chloride. The florisil was suspended in 500 ml of methanol and transferred to a column. The column was washed with an additional 500 ml of methanol. Concentration in vacuo of the combined methanol effluents gave 7.6 g of dark oil which was chromatographed on a 100 g alumina column by eluting with a 0–5% methanol/acetonitrile gradient. The first 2 fractions were discarded and the remainder combined and concentrated to an oil (5.2 g). The oil was dissolved in ethyl ether, filtered to remove traces of alumina, concentrated in vacuo and excess solvent removed by pumping under high vacuum at 55° C. for 18 hours.

Analysis: Calculated for $C_{19}H_{29}N_3O_2Cl_2$: C,56.77; H,7.27; N,10.44. Found: C,56.37; H,7.22; N,10.09.

EXAMPLE 18

4-(3,4-Dichlorophenoxy)-N-[2-(dimethylamino)ethyl]-1-piperidinecarboxamide ethanedioate A stirred solution of 18.5 g (0.06 mole) of 4-(3,4-dichlorophenoxy)-1-piperidinecarbonyl chloride in 150 ml of tetrahydrofuran was treated with 8 g (0.09 mole) of N,N-dimethylethylenediamine added all at once (the reaction was exothermic but did not reflux). After stirring overnight at ambient temperature, the mixture was filtered and the filtrate concentrated in vacuo to yield 30 g of viscous oil. A methylene chloride solution of the oil was washed with 3N sodium hydroxide, dried over magnesium sulfate and concentrated in vacuo to give 20.2 g of oil. The oxalate salt was formed in acetone but no solid product was obtained. The salt was converted back to the free base and chromatographed on a 400 g alumina column and eluted with methylene chloride and a ethyl acetate/methylene chloride gradient. Three main fractions were obtained. The first was the purest and samples of it were used to form the oxalate and hydrochloride salts. The hydrochloride salt was hygroscopic, m.p. 83°–120° C. with degassing. The oxalate salt was a granular solid. The 3 fractions were combined in acetone and treated with oxalate acid to give 16 g of white granular oxalate salt, m.p. 132°–135° C. (degasses). NMR spectrum showed approximately 0.5 mole of acetone. The sample was dried at 56° C. for 4 hours under reduced pressure (m.p. 182°–183° C.).

Analysis: Calculated for $C_{16}H_{23}N_3O_2Cl_2 \cdot C_2H_2O_4$: C,48.01; H,5.60; N,9.33. Found C,48.21; H,5.66; N,9.27.

EXAMPLE 19

3-(3,5-Dichlorophenoxy)-N-[2-diethylamino)ethyl]-1-pyrrolidinecarboxamide ethanedioate A stirred solution of 7 g (0.024 mole) of 3-(3,5-dichlorophenoxy)-1-pyrrolidinecarbonyl chloride in 70 ml of tetrahydrofuran was treated all at once with 6 g (0.05 mole) of N,N-diethylethylenediamine and stirred at ambient temperature for 18 hours. The reaction was diluted with ice water and extracted with 2×100 ml of benzene. The benzene extracts were combined, dried over magnesium sulfate, and concentrated in vacuo to give a pale yellow oil, 7.34 g. The oil in 20 ml of acetone was treated with 1.8 g of oxalic acid. The mixture was heated and then filtered to remove a fine gel. The filtrate was diluted with isopropyl ether to give a precipitate which was redissolved by the addition of heat and more acetone. Upon cooling overnight, the solution yielded 6.1 g of white amorphous powder which was hygroscopic. The solid product was dried at 68° C. under reduced pressure for 24 hours (m.p. 83°–86° C. degasses above 135° C.).

Analysis: Calculated for $C_{17}H_{25}N_3O_2Cl_2 \cdot C_2H_2O_4$: C,49.15; H,5.86; N,9.05. Found C,48.95; H,5.81; N,9.09.

EXAMPLE 20

N-[2-(Diethylamino)ethyl]-3-phenoxy-1-pyrrolidinecarboxamide

A stirred solution of 22 g (0.085 mole) 3-phenoxy-1-pyrrolidinecarbonyl chloride in 100 ml of tetrahydrofuran was cooled to 0° C., treated with 25 g of ice, 11.8 g (0.085 mole) of potassium carbonate and 9.9 g (0.085 mole) of N,N-diethylethylenediamine and stirred at ambient temperature for 18 hours. The reaction mixture was diluted with 100 ml of benzene and the aqueous layer separated. The organic layer was dried over magnesium sulfate and concentrated in vacuo to give 13.6 g of oil. An attempt to prepare a crystalline oxalate salt failed and the free base was regenerated by proportioning between methylene chloride and aqueous base. A solution of the residual oil in methylene chloride was treated with 200 g of florisil, stirred for 30 minutes and filtered. The florisil residue was washed with 3 volumes of methylene chloride, suspended in 500 ml of methanol, drained through a filter column and washed with 2 volumes of methanol. The methanol washes were combined and concentrated in vacuo to give 9 g of oil. The oil was chromatographed on a 200 g alumina column with acetonitrile to give 3.3 g of product, which was dissolved in ethyl ether and filtered to remove traces of insoluble alumina. The oil was placed in a drying pistol at 56° C. under reduced pressure (vacuum pump) overnight. White powder crystals had sublimed on the walls of the drying pistol. (Carbonate salt of diamine starting material). The column was eluted with 0–5% methanol/acetonitrile gradient to give 2.6 g of additional product which was treated the same as the above. A sample of the second oil was submitted for elemental analysis.

Analysis: Calculated for $C_{17}H_{27}N_3O_2$: C,66.85; H,8.91; N,13.76; Found: C,64.43; H,8.89; N,13.33.

EXAMPLE 21

N-[2-(Dimethylamino)ethyl]-N-ethyl-3-phenoxy-1-pyrrolidinecarboxamide

A stirred solution of 22 g (0.085 mole) of 3-phenoxy-1-pyrrolidinecarbonyl chloride in 100 ml of tetrahydrofuran was cooled to 0° C., treated with ice (25 g), 11.8 g (0.085 mole) of potassium carbonate, 12.3 g (0.085 mole) of N,N'-triethylethylenediamine, and stirred at ambient temperature for 18 hours. The reaction mixture was diluted with 100 ml of benzene and the organic phase separated, dried over magnesium sulfate and concentrated in vacuo to give 14.1 g of oil. A solution of the oil in 25 ml of acetone was treated with 3.8 g of oxalic acid, heated to reflux, diluted with an additional 25 ml of acetone and filtered to give 3.0 g of white amorphous solid, the oxalate salt of the starting diamine. The filtrate was diluted with isopropyl ether and an oil separated which did not crystallize. It was converted to the free base and slurried with 100 g of florisil in methylene chloride for 1 hour. The florisil was removed by filtration, washed with 2 volumes of methylene chloride, suspended in 500 ml of methanol, drained through a filter column and washed with 2 volumes of methanol. The methanol washes were combined and concentrated to give 8.1 g of oil. The oil was chromatographed on a 200 g alumina column by eluting with a 0–100% methanol)acetonitrile gradient to give 12-100 ml fractions. The middle 5 fractions (4-8) were combined to give 3.8 g of amber oil. The oil was heated at 55° C. for 8 hours under reduced pressure.

Analysis: Calculated for $C_{19}H_{31}N_3O_2$: C,68.43; H,9.37; N,12.60. Found: C,67.66; H,9.35; N,12.52.

EXAMPLE 22

N-[2-(Dimethylamino)ethyl]-3-(3-methylphenoxy)-1-pyrrolidinecarboxamide Ethanedioate Hemihydrate A stirred solution of 6.07 g (0.025 mole) of 3-(3-methylphenoxy)-1-pyrrolidinecarbonyl chloride in 20 ml of tetrahydrofuran was treated with 3.88 g (0.44 mole) of N,N-dimethylethylenediamine added all at once. This reaction was exothermic and had to be cooled in an ice bath. Tetrahydrofuran (100 ml) was added to facilitate stirring of this viscous material and stirring continued for 18 hours at ambient temperature. The mixture was diluted with ice water to be a volume of 600 ml and extracted with 3×100 ml of benzene. The benzene extracts were combined, washed with 50 ml of water, and dried by passing through Whatman PS filter paper. The benzene solution was chromatographed on a 200 g alumina column by eluting first with benzene then a methanol/benzene gradient (0.5–10%). The major product portion was eluted in one fraction to give 5.9 g of dark yellow oil. This oil in 20 ml of isopropanol was treated with 2 g of oxalic acid and heated to dissolve all the material. Dilution with isopropyl ether gave a precipitate which was like a wet gel. This gel under reduced pressure lost 10 times its volume as it dried to leave 0.6 g of white amorphous powder, m.p. 83°–86° C.

Analysis: Calculated for $C_{16}H_{25}N_3O_2.C_2H_2O_4.0.5\text{-}H_2O$: C,55.37; H,7.23; N,10.76. Found C,55.48; H,7.03; N,10.73.

EXAMPLE 23

N-[2-(Diethylamino)ethyl]-3-(3-methylphenoxy)-1-pyrrolidinecarboxamide ethanedioate [1:2]

A stirred solution of 6.07 g (0.025 mole) of 3-(3-methylphenoxy)-1-pyrrolidinecarbonyl chloride in 30 ml of tetrahydrofuran was cooled to 10° C. before treating with 5.1 g (0.044 mole) of N,N-diethylethylenediamine. In spite of the cooling, the reaction was exothermic and refluxed. After reaction subsided, the mixture stirred for 18 hours, diluted with ice water to 500 ml and extracted with 3×100 ml of benzene. The extracts were combined, washed with 100 ml of water, dried over magnesium sulfate and treated with 4 g of oxalic acid. The benzene mixture was heated at reflux and the benzene was decanted off. The solid residue was triturated with 100 ml of warm isopropanol and filtered to give 5.1 g of tan solid, m.p. 118°–120° C. The filtrate on cooling gave an additional 1.3 g, m.p. 119°–120° C. Recrystallization from isopropanol gave 4.1 g of pale beige crystals, m.p. 122°–123° C.

Analysis: Calculated for $C_{18}H_{29}N_3O_2.2C_2H_2O_4$: C,52.90; H,6.66; N,8.41. Found: C,52.91; H,6.69; N,8.39.

EXAMPLE 24

3-(3-Bromophenoxy)-N-[2-(dimethylamino)ethyl]-1-pyrrolidinecarboxamide ethanedioate A stirred solution of 10 g (0.023 mole) of 3-(3-bromophenoxy)-1-pyrrolidinecarbonyl chloride in 30 ml of tetrahydrofuran was cooled to 0° C. in an ice bath as 4.1 g (0.046 mole) of N,N-dimethylethylenediamine was added all at once. After stirring for 4 hours at ambient temperature, the reaction mixture was concentrated in vacuo to an oil which was dissolved in 100 ml of benzene, washed with 3×20 ml of water, dried over magnesium sulfate and after removing the drying agent, treated with 4 g of oxalic acid. The benzene was decanted and most of the solid material dissolved in refluxing isopropanol. Filtration removed some amorphous material and the filtrate was diluted with isopropyl ether. After cooling overnight in a refrigerator, filtration gave 5 g of fine crystalline powder which was dried for 3.5 hours at 56° C. under reduced pressure, m.p. 78°–86° C.

Analysis: Calculated for $C_{15}H_{22}BrN_3O_2.C_2H_2O_4$: C,45.75; H,5.42; N,9.42. Found C,45.91; H,5.46; N,9.43.

EXAMPLE 25

3-(3-Bromophenoxy)-N-[2-(diethylamino)ethyl]-1-pyrrolidinecarboxamide Ethanedioate (1:2)

A stirred solution of 10 g (0.023 mole) of 3-(3-bromophenoxy)-1-pyrrolidinecarbonyl chloride in 50 ml of tetrahydrofuran was cooled to 10° C., treated with 3.4 g (0.046 mole) of N,N-diethylethylenediamine added all at once and stirred for 18 hours at ambient temperature. The solvent was removed in vacuo and the oily residue triturated with 3×50 ml of warm water. After decanting the water, the residue was dissolved in acetone and treated with 4 g of oxalic acid. The acetone was decanted and the residual solid recrystallized from isopropanol/isopropyl ether to give a rose crystalline product which appears somewhat tacky, 7.8 g. The crude product was dissolved in isopropanol, treated with charcoal, filtered through celite and the filtrate cooled to yield 4.8 g of white granular product which was dried overnight at 82° C. under reduced pressure, m.p. 113°–115° C.

Analysis: Calculated for $C_{17}H_{26}BrN_3O_2.2C_2H_2O_4$: C, 44.690; H,5.358; N,7.445. Found C,45.05; H,5.45; N,7.50.

EXAMPLE 26

N-[2-(Dimethylamino)ethyl]-3-(2-methoxyphenoxy)-1-pyrrolidinecarboxamide Ethanedioate, Hemihydrate A stirred solution of 22.2 g (0.087 mole) of 3-(2-methoxyphenoxy)-1-pyrrolidinecarbonyl chloride in 75 ml of tetrahydrofuran was treated with 15.5 g (0.175 mole) of N,N-dimethylethylenediamine, stirred for 3 hours at ambient temperature, diluted with ice water and extracted with 5×50 ml of benzene. The benzene extracts were combined, dried over magnesium sulfate and concentrated in vacuo to give 20 g of dark oil. TLC (5% methanol/methylene chloride; alumina) showed 1 major spot for product and 4 other minor spots. The oil was chromatographed on a 200 g alumina column with methylene chloride as the elution solvent to give 9.2 g of crude product (contains 3 of the minor spots by TLC). The elution was continued with a methanol/methylene chloride gradient (0.5–5%) to give 2 major fractions containing 6.58 g and 3.25 g respectively. The smaller fraction contains an impurity (by TLC). The 6.58 g fraction was converted to the oxalate salt in acetone to give a fine white crystalline product which was extremely hygroscopic. The oxalate salt was converted back to the free base. The oil was dissolved in methylene chloride and stirred overnight with 100 g of florisil. The methylene chloride was removed by filtration, the florisil residue washed with methylene chloride and air dried. The florisil was suspended in 200 ml of methanol, filtered, washed with additional methanol and the combined methanol filtrates concentrated in vacuo to an oil. The oil was dissolved in benzene (50 ml) and reconcentrated twice to azeotrope the methanol. The oil residue was placed under reduced pressure for several days. NMR shows 1 mole of benzene which was not removed when heated at 100° C. under reduced pressure. This oil in tetrahydrofuran was converted to the oxalate salt and crystallized on adding ethyl ether to give 2.4 g of fine white powder which was dried under reduced pressure, m.p. 58°–70° C.

Analysis: Calculated for $C_{16}H_{25}N_3O_3.C_2H_2O_4.0.5-H_2O$: C,53.19; H,6.94; N,10.33. Found C,53.41; H,6.99; N,10.00.

EXAMPLE 27

3-[(2,3-Dihydro-1H-inden-4-yl)oxy]-N-[2-(dimethylamino)ethyl]-1-pyrrolidinecarboxamide Ethanedioate Hemihydrate A stirred solution of 6.1 g (0.023 mole) of 3-1H-indanyloxy)-1-pyrrolidinecarbonyl chloride in 30 ml of tetrahydrofuran was cooled to 10° C., treated with 4.1 g (0.046 mole) of N,N-dimethylethylenediamine and stirred at ambient temperature overnight. The reaction was diluted to 600 ml with ice water and extracted with 3×200 ml portions of benzene. The combined benzene extracts were washed with 2×300 ml portions of ice water and dried by passing through Whatman PS filter paper. The benzene solution was treated with 3.8 g of oxalic acid, heated to boiling, cooled and the benzene decanted. The solid residue was recrystallized from isopropyl alcohol after treating with charcoal to give 8.3 g of granular solid which was dried at 56° C. under reduced pressure for 18 hours, m.p. 71°–77° C. Elemental analysis was quite low and the solid material along with filtrate residues were combined, concentrated to an amber oil (9.1 g) and recrystallized from methyl ethyl ketone to give 7.2 g of beige crystalline product, m.p. 89°–98° C. The sample was dried at 82° C. for 6 hours under reduced pressure; no change in melting point. The solid was resubmitted for elemental analysis. Elemental analysis and NMR spectral data identified it as the hemihydrate of the oxalate salt.

Analysis: Calculated for $C_{18}H_{27}N_3O_2.C_2H_2O_4.0.5-H_2O$: C,57.68; H,7.26; N,10.09. Found C,58.07; H,7.27; N,9.87.

EXAMPLE 28

3-[(2,3-Dihydro-1H-inden-4-yl)oxy]-N-[2-(diethylamino)ethyl]-1-pyrrolidinecarboxamide Ethanedioate, Hydrate A stirred solution of 6.1 g (0.023 mole) of 3-(4-indanyloxy)-1-pyrrolidinecarbonyl chloride in 30 ml of tetrahydrofuran was cooled to 10° C., treated with 5.3 g (0.046 mole) of N,N-diethylethylenediamine, and stirred at ambient temperature overnight. The mixture was diluted with 600 ml of ice water and extracted with 3×200 ml of benzene. The benzene extracts were combined, dried by passing through Whatman PS filter paper and treated with 3.8 g of oxalic acid. The benzene was decanted from the solid residue which was recrystallized from isopropanol with difficulty to give 5.8 g of tan amorphous powder. It was dried at 56° C. under reduced pressure for 18 hours and melted at 98°–102° C. The filtrate was concentrated to a solid which was combined with the 5.8 g portion and recrytallized from methylethyl ketone to give 5 g of fine white crystalline powder, m.p. 96°–99° C. which was submitted for elemental analysis after drying for 8 hours at 82° C., m.p. 116°–120° C.

Analysis: Calculated for $C_{20}H_{31}N_3O_2.C_2H_2O_4.H_2O$: C,58.26; H,7.779; N,9.26. Found: C,58.70; H,7.53; N,9.00.

EXAMPLE 29

3-[(2,3-Dihydro-1H-inden-5-yl)oxy]-N-[2-(dimethylamino)ethyl]-1-pyrrolidinecarboxamide Utilizing the procedure of Example 27, the title compound is prepared by reacting 3-(5-indanyloxy)-1-pyrrolidinecarbonyl chloride with N,N-dimethylethylenediamine. The oxalate salt may be prepared for ease of purification and converted back to the free base by proportioning procedures, known for isolating a free base from an acid addition salt as described above.

EXAMPLE 30

N-[2-(Dimethylamino)ethyl]-3-(1-naphthylenyloxy)-1-pyrrolidinecarboxamide Oxalate Hydrate Following the procedure of Example 27, 3-[3-(1-naphthalenyloxy)]-1-pyrrolidinecarbonyl chloride is reacted with N,N-dimethylethylenediamine and oxalic acid.

EXAMPLE 31

N-[2-(Dimethylamino)ethyl]-3-(2-naphthalenyloxy)-1-pyrrolidinecarboxamide Oxalate Hydrate Following the procedure of Example 27, 3-[3-(2-naphthalenyloxy)]-1-pyrrolidinecarbonyl chloride is reacted with N,N-dimethylenediamine and oxalic acid.

EXAMPLE 32

When in the procedure of Example 1 the following are reacted with N,N-dimethylethylenediamine followed by oxalic acid:
3-(3-ethylphenoxy)-1-pyrrolidinecarbonyl chloride,
3-[3-(trifluoromethyl)phenoxy]-1-pyrrolidinecarbonyl chloride, and
3-[4-(trifluoromethyl)phenoxy]-1-pyrrolidinecarbonyl chloride,
there are obtained:
N-[2-(dimethylamino)ethyl]-3-(3-ethylphenoxy)-1-pyrrolidinecarboxamide oxalate,
N-[2-(dimethylamino)ethyl]-3-[3-(trifluoromethyl)phenoxy]-1-pyrrolidinecarboxamide oxalate, and
N-[2-(dimethylamino)ethyl]-3-[4-(trifluoromethyl)phenoxy]-1-pyrrolidinecarboxamide oxalate,

EXAMPLE 33

3-(3-Chloro-4-fluorophenoxy)-N-[2-dimethylamino)ethyl]-1-pyrrolidinecarboxamide Oxalate.

The title compound is prepared from 3-(chloro-4-fluorophenoxy)-1-pyrrolidinecarbonyl chloride, N,N-dimethylethylenediamine and oxalic acid utilizing the technique employed in Example 1.

EXAMPLE 34

When in the procedure of Example 1 the following are substituted for 3-(3-chlorophenoxy)-1-pyrrolidinecarbonyl chloride:
3-(2-methylphenoxy)-1-pyrrolidinecarbonyl chloride,
3-(2-ethoxyphenoxy)-1-pyrrolidinecarbonyl chloride,
3-(4-methoxyphenoxy)-1-pyrrolidinecarbonyl chloride,
3-(4-fluorophenoxy)-1-pyrrolidinecarbonyl chloride,
3-(3,5-dimethylphenoxy)-1-pyrrolidinecarbonyl chloride,
3-(3-methoxyphenoxy)-1-pyrrolidinecarbonyl chloride,
3-(4-chlorophenoxy)-1-pyrrolidinecarbonyl chloride,
3-(4-bromophenoxy)-1-pyrrolidinecarbonyl chloride,
3-(3,5-dimethoxyphenoxy)-1-pyrrolidinecarbonyl chloride,
these are obtained:
(a) N-[2-(dimethylamino)ethyl]-3-(2-methylphenoxy)-1-pyrrolidinecarboxamide oxalate,
(b) N-[2-(dimethylamino)ethyl]-3-(2-ethoxyphenoxy)-1-pyrrolidinecarboxamide oxalate,
(c) N-[2-(dimethylamino)ethyl]-3-(4-methoxyphenoxy)-1-pyrrolidinecarboxamide oxalate,
(d) N-[2-(dimethylamino)ethyl]-3-(4-fluorophenoxy)-1-pyrrolidinecarboxamide oxalate,
(e) N-[2-(dimethylamino)ethyl]-3-(3,5-dimethylphenoxy)-1-pyrrolidinecarboxamide oxalate,
(f) 3-(4-chlorophenoxy)-N-[2-(dimethylamino)ethyl]-1-pyrrolidinecarboxamide oxalate,
(g) 3-(4-bromophenoxy)-N-[2-(dimethylamino)ethyl]-1-pyrrolidinecarboxamide oxalate, and
(h) N-[2-(dimethylamino)ethyl]-3-(3,5-dimethoxyphenoxy)-1-pyrrolidinecarboxamide oxalate.

EXAMPLE 35

When in the procedure of Example 18 the following are substituted for 4-(3,4-dichlorophenoxy)-1-piperidinecarbonyl chloride:
4-(4-bromophenoxy)-1-piperidinecarbonyl chloride,
4-(phenoxy)-1-piperidinecarbonyl chloride,
4-(3-trifluoromethylphenoxy)-1-piperidinecarbonyl chloride,
4-(4-trifluoromethylphenoxy)-1-piperidinecarbonyl chloride,
these are obtained:
(a) 4-(4-bromophenoxy)-N-[2-(dimethylamino)ethyl]-1-piperidinecarboxamide oxalate,
(b) N-[2-(dimethylamino)ethyl]-4-phenoxy-1-piperidinecarboxamide oxalate,
(c) N-[2-(dimethylamino)ethyl]-4-(3-trifluoromethylphenoxy)-1-piperidinecarboxamide oxalate, and
(d) N-[2-(dimethylamino)ethyl]-4-(4-trifluoromethylphenoxy-1-piperidinecarboxamide oxalate.

EXAMPLE 36 (a to t)

When in the procedure of Example 1 the following are substituted for 3-(3-chlorophenoxy)-1-pyrrolidinecarbonyl chloride:
3-(3-methylphenoxy)-1-pyrrolidinecarbothioyl chloride,
3-(2-methoxyphenoxy)-1-pyrrolidinecarbothioyl chloride,
3-(3-chloro-4-fluorophenoxy)-1-pyrrolidinecarbothioyl chloride,
3-(3,4-dichlorophenoxy)-1-pyrrolidinecarbothioyl chloride,
3-(3,5-dichlorophenoxy)-1-pyrrolidinecarbothioyl chloride,
3-(4-indanyloxy)-1-pyrrolidinecarbothioyl chloride,
3-(1-naphthalenyloxy)-1-pyrrolidinecarbothioyl chloride,
3-(3-chlorophenoxy)-1-pyrrolidinecarbothioyl chloride,
3-(2,6-dichlorophenoxy)-1-pyrrolidinecarbothioyl chloride,
3-(2,3-dichlorophenoxy)-1-pyrrolidinecarbothioyl chloride,
3-(3-bromophenoxy)-1-pyrrolidinecarbothioyl chloride,
3-(phenoxy)-1-pyrrolidinecarbothioyl chloride,
3-(5-indanyloxy)-1-pyrrolidinecarbothioyl chloride,
3-(2-naphthalenyloxy-1-pyrrolidinecarbothioyl chloride,
3-(3-ethylphenoxy)-1-pyrrolidinecarbothioyl chloride, 3-[3-(trifluoromethyl)phenoxy]-1-pyrrolidinecarbothioyl chloride,
3-[4-(trifluoromethyl)phenoxy]-1-pyrrolidinecarbothioyl chloride,
3-(4-chlorophenoxy)-1-pyrrolidinecarbothioyl chloride,
3-(3,4-dichlorophenoxy-1-piperidinecarbothioyl chloride, and
4-(3,4-dichlorophenoxy-1-piperidinecarbothioyl chloride,
there are obtained oxalate salts of the following:
  (a) N-[2-(dimethylamino)ethyl]-3-(3-methylphenoxy)-1-pyrrolidinecarbothioamide,
  (b) N-[2-(dimethylamino)ethyl]-3-(2-methoxyphenoxy)-1-pyrrolidinecarbothioamide,
  (c) 3-(3-chloro-4-fluorophenoxy)-N-[2-(dimethylamino)ethyl]-1-pyrrolidinecarbothioamide,
  (d) 3-(3,4-dichlorophenoxy)-N-[2-(dimethylamino)ethyl]-1-pyrrolidinecarbothioamide,
  (e) 3-(3,5-dichlorophenoxy)-N-[2-(dimethylamino)ethyl]-1-pyrrolidinecarbothioamide,
  (f) N-[2-(dimethylamino)ethyl]-3-[(2,3-dihydro-1H-inden-4-yl)oxy]-1-pyrrolidinecarbothioamide,
  (g) N-[2-(dimethylamino)ethyl]-3-(1-naphthalenyloxy)-1-pyrrolidinecarbothioamide,
  (h) 3-(3-chlorophenoxy)-N-[2-(dimethylamino)ethyl]-1-pyrrolidinecarbothioamide,
  (i) 3-(2,6-dichlorophenoxy)-N-[2-(dimethylamino)ethyl]-1-pyrrolidinecarbothioamide,
  (j) 3-(2,3-dichlorophenoxy)-N-[2-(dimethylamino)ethyl]-1-pyrrolidinecarbothioamide,
  (k) 3-(3-bromophenoxy)-N-[2-(dimethylamino)ethyl]-1-pyrrolidinecarbothioamide,
  (l) N-[2-(dimethylamino)ethyl]-3-phenoxy-1-pyrrolidinecarbothioamide,
  (m) N-[2-(dimethylamino)ethyl]-3-[(2,3-dihydro-1H-inden-5-yl)oxy]-1-pyrrolidinecarbothioamide,
  (n) N-[2-(dimethylamino)ethyl]-3-(2-naphthalenyloxy)-1-pyrrolidinecarbothioamide,
  (o) N-[2-(diethylamino)ethyl]-3-(3-ethylphenoxy)-1-pyrrolidinecarbothioamide,
  (p) N-[2-(dimethylamino)ethyl]-3-[3-(trifluoromethyl)phenoxy]-1-pyrrolidinecarbothioamide,
  (q) N-[2-(dimethylamino)ethyl]-3-[4-(trifluoromethyl)phenoxy]-1-pyrrolidinecarbothioamide,
  (r) 3-(4-chlorophenoxy)-N-[2-(dimethylamino)ethyl]-1-pyrrolidinecarbothioamide,
  (s) 3-(3,4-dichlorophenoxy)-N-[2-(dimethylamino)ethyl]-1-piperidinecarbothioamide, and
  (t) 4-(3,4-dichlorophenoxy)-N-[2-(dimethylamino)ethyl]-1-piperidinecarbothioamide.

EXAMPLE 37

When in the procedure of Example 20 the following are reacted with 3-phenoxypyrrolidinecarbonyl chloride:
N-(2-aminoethyl)morpholine,
N-(2-aminoethyl)pyrrolidine,
N-(2-aminoethyl)piperidine,
1-(2-aminoethyl)-4-methylpiperazine, and
1-(2-aminoethyl)-4-(t-butoxycarbonyl)piperazine,
there are obtained:
N-[2-(4-morpholinyl)ethyl]-3-phenoxy-1-pyrrolidinecarboxamide,
N-[2-(1-pyrrolidinyl)ethyl]-3-phenoxy-1-pyrrolidinecarboxamide,
N-[2-(1-piperidinyl)ethyl]-3-phenoxy-1-pyrrolidinecarboxamide,
N-[2-(4-methyl-1-piperazinyl)ethyl]-3-phenoxy-1-pyrrolidinecarboxamide, and
N-[2-(4-t-butoxycarbonyl)-1-piperazinyl)ethyl]-1-pyrrolidinecarboxamide.

Pharmaceutical Compositions

The invention further provides antiarrhythmia compositions for administration to living mammals such as humans comprising, as active ingredients, at least one of the compounds according to the invention in association with a pharmaceutical carrier or excipient.

The compounds are presented in a form suitable for oral, rectal, parenteral or intracardial administration. Thus, for example, compositions for oral administration are preferably solids and can take the form of capsules, tablets or coated tablets containing carriers conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampules. Exemplary of liquid carriers for oral administration are vegetable oils and water.

In compositions for rectal administration the carrier can comprise a suppository base, e.g., cocoa butter, or a glyceride.

Advantageously, the compositions are formulated as dosage units, each unit being adapted to supply a fixed dose of active ingredients. Tablets, coated tablets, capsules, ampules and suppositories are examples of preferred dosage forms according to the invention. It is only necessary that the active ingredient constitute an effective amount, i.e., such that a suitable effective dosage will be obtained consistent with the dosage form employed. The exact individual dosages, as well as daily dosages, will, of course, be determined according to standard medical principles under the direction of a physician or veterinarian. Generally, the pharmacology on animals suggests that the oral dosage effective to correct arrhythmias will be about 3 times that of the intravenous dosage.

Based on the animal data, allowing for variation in species and severity of cardiac arrhythmia, unit dosages containing an amount of compound equivalent to about 1 to about 100 mg/kg of body weight are contemplated. Based on all of the above considerations, a choice in a range of unit oral dosages for humans of about 10 to about 1000 mg is contemplated, preferably about 10 to 600 mg. Daily dosages of about 30 to 2400 mg are contemplated for humans and obviously several unit dosage forms may be administered at about the same time. However, the scope of the invention is not to be limited by these contemplations due to the uncertainty in transpositions discussed above.

Examples of compositions within the preferred ranges given are as follows:

| Capsules | |
|---|---|
| Ingredients | Per Cap |
| 1 Active ingredient | 10.0 mg. |
| 2 Lactose | 146.0 mg. |
| 3 Magnesium Stearate | 4.0 mg. |

Procedure
1. Blend 1, 2 and 3.
2. Mill this blend and blend again.
3. This milled blend is then filled into #1 hard gelatin

| Tablets (10 mg) | |
| --- | --- |
| Ingredients | Mg/Tab |
| 1. Active ingredient | 10.0 mg |
| 2. Corn Starch | 20.0 mg |
| 3. Kelacid | 20.0 mg |
| 4. Keltose | 20.0 mg |
| 5. Magnesium Stearate | 1.3 mg |

| Tablets (50 mg) | |
| --- | --- |
| Ingredients | Mg/Tab. |
| 1. Active ingredient | 50.0 mg. |
| 2. Milo starch | 20.0 mg. |
| 3. Corn starch | 38.0 mg. |
| 4. Lactose | 90.0 mg. |
| 5. Calcium stearate | 2.0 mg. |
| | 200.0 mg. |

Procedure
1. Blend 1, 2, 3 and 4.
2. Add sufficient water portionwise to the blend from step #1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

| Intravenous Injection | |
| --- | --- |
| Ingredients | Per ml. |
| 1. Active ingredient | 1.0 mg. |
| 2. pH 4.0 Buffer solution | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Intramuscular Injection | |
| --- | --- |
| Ingredients | Per ml. |
| 1. Active ingredient | 5.0 mg. |
| 2. Isotomic Buffer solution 4.0 | q.s. to 1.0 ml. |

Procedure
1. Dissolve the active ingredient in the buffer solution.
2. Aseptically filter the solution from step #1.
3. The sterile solution is now aseptically filled into sterile ampuls.
4. The ampuls are sealed under aseptic conditions.

| Suppositories | |
| --- | --- |
| Ingredients | Per Supp. |
| 1. Active ingredient | 10.0 mg. |
| 2. Polyethylene Glycol 1000 | 1350.0 mg. |
| 3. Polyethylene Glycol 4000 | 450.0 mg. |

Procedure
1. Melt 2 and 3 together and stir until uniform.
2. Dissolve #1 in the molten mass from step 1 and stir until uniform.
3. Pour the molten mass from step 2 into suppository molds and chill.
4. Remove the suppositories from molds and wrap.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A method for the treatment of cardiac arrhythmia in a patient consisting essentially of administering a cardiac arrhythmia inhibiting quantity of a compound of the formula:

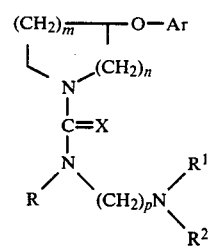

wherein
Ar is selected from the group consisting of 1-naphthyl, 2-naphahyl, 2,3-dihydro-1H-inden-4-yl, 2,3-dihydro-1H-inden-5-yl, phenyl, substituted phenyl wherein the substituents are selected from lower alkyl of from 1 to 8 carbon atoms, lower alkyloxy of from 1 to 8 carbon atoms, halogen and trifluoromethyl;
m and n are 1 or 2 but are never 2 at the same time;
p is 1, 2, 3 or 4;
R is selected from hydrogen or lower alkyl of from 1 to 3 carbon atoms;
$R^1$ and $R^2$ are selected from hydrogen, lower alkyl of from 1 to 8 carbon atoms, phenyl, phenyl lower alkyl of from 7 to 9 carbon atoms, and cycloalkyl of from 3 to 8 carbon atoms, and $R^1$ and $R^2$ taken together with the adjacent atom may form a heterocyclic residue selected from 4-morpholino, 1-pyrrolidino, 1-piperidino, 1-piperazino and 4-lower alkyl piperazin-1-yl;
X is oxygen or sulfur; and the pharmaceutically acceptable acid addition salts thereof.

2. The method of claim 1 wherein Ar is phenyl.

3. The method of claim 1 wherein Ar is substituted phenyl.

4. The method of claim 3 wherein Ar is halo-substituted phenyl.

5. The method of claim 1 wherein X is oxygen.

6. The method of claim 1 wherein R is hydrogen.

7. The method of claim 1 wherein $R^1$ and $R^2$ are each lower alkyl.

8. The method of claim 1 wherein $R^1$ and $R^2$ are each methyl.

9. The method of claim 1 wherein said compound is 3-(3-chlorophenoxy)-N-[2-(dimethylamino)ethyl]-1-pyrrolidine carboxamide or a pharmaceutically acceptable acid addition salt thereof.

10. The method of claim 1 wherein said compound is 3-(3,5-dichlorophenoxy)-N-[2-(dimethylamino)ethyl]-1-pyrrolidine carboxamide or a pharmaceutically acceptable acid addition salt thereof.

11. The method of claim 1 wherein said compound is 3-(2,6-dichlorophenoxy)-N-[3-(dimethylamino)propyl]-1-pyrrolidine carboxamide or a pharmaceutically acceptable acid addition salt thereof.

12. The method of claim 1 wherein said compound is 3-(2,3-dichlorophenoxy)-N-(2-dimethylaminoethyl)-1-pyrrolidine carboxamide or a pharmaceutically acceptable acid addition salt thereof.

13. The method of claim 1 wherein said compound is 3-(2,3-dichlorophenoxy)-N-[3-(dimethylamino)propyl]-1-pyrrolidine carboxamide or a pharmaceutically acceptable acid addition salt thereof.

14. The method of claim 1 wherein said compound is 3-(3-chlorophenoxy)-N-[3-(dimethylamino)propyl]-1-pyrrolidine carboxamide or a pharmaceutically acceptable acid addition salt thereof.

15. The method of claim 1 wherein said compound is 3-(3-dichlorophenoxy)-N-[2-(dimethylamino)propyl]-1-pyrrolidine carboxamide or a pharmaceutically acceptable acid addition salt thereof.

16. The method of claim 1 wherein said compound is 3-(3,5-dichlorophenoxy)-N-[3-(dimethylamino)propyl]-1-pyrrolidine carboxamide or a pharmaceutically acceptable acid addition salt thereof.

17. The method of claim 1 wherein said compound is N-[2-(dimethylamino)ethyl]-3-phenoxy-1-pyrrolidine carboxamide or a pharmaceutically acceptable acid addition salt thereof.

18. The method of claim 1 wherein said compound is 3-(3-chlorophenoxy)-N-[2-(dimethylamino)ethyl]-N-methyl-1-pyrrolidine carboxamide or a pharmaceutically acceptable acid addition salt thereof.

19. The method of claim 1 wherein said compound is 3-(3,4-dichlorophenoxy)-N-[2-(dimethylamino)ethyl]-1-pyrrolidine carboxamide or a pharmaceutically acceptable acid addition salt thereof.

20. The method of claim 1 wherein said compound is 3-(3,4-dichlorophenoxy)-N-[2-(dimethylamino)ethyl]-1-piperidine carboxamide or a pharmaceutically acceptable acid addition salt thereof.

21. The method of claim 1 wherein said compound is 4-(3,4-dichlorophenoxy)-N-[2-(dimethylamino)ethyl]-N-methyl-1-piperidine carboxamide or a pharmaceutically acceptable acid addition salt thereof.

* * * * *